US012576013B2

(12) United States Patent
Song

(10) Patent No.: US 12,576,013 B2
(45) Date of Patent: Mar. 17, 2026

(54) DISSOLVABLE SOLID FIBROUS SHAMPOO ARTICLES CONTAINING SALTS

(71) Applicant: The Procter & Gamble Company, Cincinnati, OH (US)

(72) Inventor: Brian Xiaoqing Song, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 490 days.

(21) Appl. No.: 18/080,853

(22) Filed: Dec. 14, 2022

(65) Prior Publication Data

US 2023/0190588 A1 Jun. 22, 2023

Related U.S. Application Data

(60) Provisional application No. 63/290,653, filed on Dec. 17, 2021.

(51) Int. Cl.

| | |
|---|---|
| ***A61K 8/00*** | (2006.01) |
| ***A61K 8/02*** | (2006.01) |
| ***A61K 8/20*** | (2006.01) |
| ***A61K 8/365*** | (2006.01) |
| ***A61K 8/44*** | (2006.01) |
| ***A61K 8/73*** | (2006.01) |
| ***A61K 8/81*** | (2006.01) |
| ***A61Q 5/02*** | (2006.01) |

(52) U.S. Cl.

CPC ................ *A61K 8/027* (2013.01); *A61K 8/20* (2013.01); *A61K 8/365* (2013.01); *A61K 8/44* (2013.01); *A61K 8/731* (2013.01); *A61K 8/8129* (2013.01); *A61K 8/817* (2013.01); *A61Q 5/02* (2013.01)

(58) Field of Classification Search

None

See application file for complete search history.

(56) References Cited

U.S. PATENT DOCUMENTS

| | | | |
|---|---|---|---|
| 1,421,350 | A | 6/1922 | Powell |
| 2,356,168 | A | 8/1944 | Mabley |

(Continued)

FOREIGN PATENT DOCUMENTS

| | | | |
|---|---|---|---|
| AU | 2004202461 | B2 | 11/2007 |
| CA | 2300638 | A1 | 8/2000 |

(Continued)

OTHER PUBLICATIONS

"Prill", wikipedia, https://en.wikipedia.org/wiki/Prill, No Known Date, 1 Page.

(Continued)

*Primary Examiner* — Necholus Ogden, Jr.

(74) *Attorney, Agent, or Firm* — Alexandra S. Anoff

(57) ABSTRACT

A dissolvable solid fibrous shampoo article having a plurality of fibrous elements. The fibrous elements contain one or more polymeric structurants; one or more cationic polymers, a surfactant system, and two or more salts that include an inorganic salt and an organic salt. The plurality of fibrous elements are intertangled or otherwise associated with one another to form the fibrous article. The present invention provides a dissolvable solid fibrous shampoo articles having an adequate strength during manufacturing while not slowing down the dissolution of the structure during usage.

12 Claims, 3 Drawing Sheets

(56) References Cited

U.S. PATENT DOCUMENTS 2,396,278 A 3/1946 Otto
2,438,091 A 3/1948 Lynch
2,486,921 A 11/1949 Byerly
2,486,922 A 11/1949 Bruce
2,528,378 A 10/1950 Mannheimer
2,613,185 A 10/1952 Marshall
2,648,635 A 8/1953 Brown et al.
2,658,072 A 11/1953 Kosmin
2,694,668 A 11/1954 Fricke
2,809,971 A 10/1957 Bernstein et al.
3,152,046 A 10/1964 Kapral
3,157,611 A 11/1964 Lindemann
3,236,733 A 2/1966 Karsten et al.
3,293,718 A 12/1966 Sheets
3,321,425 A 5/1967 Blau et al.
3,332,880 A 7/1967 Kessler et al.
3,426,440 A 2/1969 Shen et al.
3,428,478 A 2/1969 Donaldson et al.
3,452,382 A 7/1969 Kazdan
3,463,308 A 8/1969 Deneke
3,489,688 A 1/1970 Pospischil
3,570,122 A 3/1971 Willimas
3,589,007 A 6/1971 Walton
3,653,383 A 4/1972 Wise
3,695,989 A 10/1972 Albert
3,753,196 A 8/1973 Kurtz et al.
3,761,418 A 9/1973 Parran
3,859,125 A 1/1975 Miller
3,875,300 A 4/1975 Homm et al.
3,904,543 A 9/1975 Knighten
3,929,678 A 12/1975 Laughlin
3,943,949 A 3/1976 Ashton et al.
3,954,113 A 5/1976 Bohrer et al.
3,957,921 A 5/1976 Iwahashi et al.
3,967,921 A 7/1976 Haberli et al.
4,020,156 A 4/1977 Murray et al.
4,024,078 A 5/1977 Gilbert et al.
4,033,365 A 7/1977 Klepak et al.
4,051,081 A 9/1977 Jabs et al.
4,089,945 A 5/1978 Brinkman et al.
4,149,551 A 4/1979 Benjamin et al.
4,180,558 A 12/1979 Franklin
4,185,125 A 1/1980 Kimura et al.
4,196,190 A 4/1980 Gehman et al.
4,197,865 A 4/1980 Jacquet et al.
4,206,196 A 6/1980 Davis
4,217,914 A 8/1980 Jacquet et al.
4,272,511 A 6/1981 Papantoniou et al.
4,286,016 A 8/1981 Dimond
4,287,219 A 9/1981 Fabre
4,315,965 A 2/1982 Mason
4,323,525 A 4/1982 Bornat
4,323,683 A 4/1982 Bolich, Jr. et al.
4,340,583 A 7/1982 Wason
4,342,813 A 8/1982 Erickson
4,345,080 A 8/1982 Bolich, Jr.
4,349,531 A 9/1982 Mlodozeniec
D266,829 S 11/1982 Yoshizawa et al.
4,377,615 A 3/1983 Suzuki
4,379,753 A 4/1983 Bolich, Jr.
4,381,919 A 5/1983 Jacquet et al.
4,415,617 A 11/1983 D'Elia
4,422,853 A 12/1983 Jacquet et al.
4,448,699 A 5/1984 Barrat et al.
4,470,982 A 9/1984 Winkler
4,507,280 A 3/1985 Pohl et al.
4,529,586 A 7/1985 De Marco et al.
4,536,361 A 8/1985 Torobin
4,565,647 A 1/1986 Llenado
D286,450 S 10/1986 Tovey
4,635,351 A 1/1987 Koch et al.
4,637,859 A 1/1987 Trokhan
4,639,390 A 1/1987 Shoji
4,663,158 A 5/1987 Wolfram et al.
4,683,001 A 7/1987 Floyd
4,710,374 A 12/1987 Grollier et al.
4,723,362 A 2/1988 Boerger
4,727,410 A 2/1988 Higgins, III
4,822,613 A 4/1989 Rodero
4,885,107 A 12/1989 Wetzel
4,892,758 A 1/1990 Serbiak
4,923,660 A 5/1990 Willenberg
4,976,953 A 12/1990 Orr et al.
4,990,280 A 2/1991 Thorengaard
5,034,421 A 7/1991 Fuisz
5,041,252 A 8/1991 Fujii
5,052,296 A 10/1991 Shiba
5,055,384 A 10/1991 Kuehnert
5,061,481 A 10/1991 Suzuki et al.
5,062,889 A 11/1991 Hoehl et al.
5,062,994 A 11/1991 Imperatori
5,094,853 A 3/1992 Hagarty
5,098,636 A 3/1992 Balk
5,100,657 A 3/1992 Ansher-jackson et al.
5,100,658 A 3/1992 Bolich, Jr. et al.
5,102,129 A 4/1992 Roberts
5,104,646 A 4/1992 Bolich, Jr.
5,106,609 A 4/1992 Bolich, Jr.
5,110,678 A 5/1992 Narukawa
5,112,515 A 5/1992 Buxton et al.
5,120,888 A 6/1992 Nohr
5,135,804 A 8/1992 Harpell
5,158,810 A 10/1992 Oishi
5,166,276 A 11/1992 Hayama et al.
D334,420 S 3/1993 Copeland et al.
5,208,104 A 5/1993 Ueda
5,220,033 A 6/1993 Kamei et al.
5,230,853 A 7/1993 Colegrove
5,261,426 A 11/1993 Kellett et al.
5,280,079 A 1/1994 Allen et al.
RE34,584 E 4/1994 Grote et al.
5,342,335 A 8/1994 Rhim
D351,345 S 10/1994 Geho
5,362,532 A 11/1994 Famili
5,364,627 A 11/1994 Song
5,387,147 A 2/1995 Ohshima
5,391,368 A 2/1995 Gerstein
D357,115 S 4/1995 Ashley et al.
5,409,703 A 4/1995 Mcanalley et al.
D358,025 S 5/1995 Martin et al.
5,415,810 A 5/1995 Lee et al.
5,429,628 A 7/1995 Trinh et al.
5,429,874 A 7/1995 Vanputte
5,444,113 A 8/1995 Sinclair et al.
5,446,079 A 8/1995 Buchanan et al.
5,455,114 A 10/1995 Ohmory
5,457,895 A 10/1995 Thompson et al.
5,458,433 A 10/1995 Stastny
5,470,424 A 11/1995 Isaac
5,470,492 A 11/1995 Childs et al.
5,470,653 A 11/1995 Honeycutt
5,476,597 A 12/1995 Sakata et al.
5,486,418 A 1/1996 Ohmory
5,501,238 A 3/1996 Borstel et al.
5,518,730 A 5/1996 Fuisz
5,520,924 A 5/1996 Chapman
5,533,636 A 7/1996 Reiker
5,538,735 A 7/1996 Ahn
5,580,481 A 12/1996 Sakata et al.
5,582,786 A 12/1996 Brunskill et al.
5,585,059 A 12/1996 Kobayashi
D378,180 S 2/1997 Hayes et al.
5,651,987 A 7/1997 Fuisz
5,660,845 A 8/1997 Trinh et al.
5,672,576 A 9/1997 Behrens et al.
5,673,576 A 10/1997 Chen et al.
5,674,478 A 10/1997 Dodd
5,691,015 A 11/1997 Tsukamoto
5,705,183 A 1/1998 Phillips
5,716,692 A 2/1998 Warner
5,717,026 A 2/1998 Ikimine
5,735,812 A 4/1998 Hardy
5,750,122 A 5/1998 Evans
5,756,438 A 5/1998 Rau et al.

(56) References Cited

U.S. PATENT DOCUMENTS

| | | | |
|---|---|---|---|
| 5,780,047 | A | 7/1998 | Kamiya et al. |
| 5,780,418 | A | 7/1998 | Niinaka |
| D398,847 | S | 9/1998 | Wyslotsky et al. |
| D399,260 | S | 10/1998 | Thimote |
| 5,827,586 | A | 10/1998 | Yamashita |
| 5,840,423 | A | 11/1998 | Sano |
| 5,840,675 | A | 11/1998 | Yeazell |
| 5,849,378 | A | 12/1998 | Gask |
| 5,863,887 | A | 1/1999 | Gillette |
| 5,879,493 | A | 3/1999 | Johnson |
| D407,640 | S | 4/1999 | Crapser et al. |
| D408,223 | S | 4/1999 | Henry |
| 5,911,224 | A | 6/1999 | Berger |
| 5,914,124 | A | 6/1999 | Mahoney |
| 5,925,603 | A | 7/1999 | D'Angelo |
| 5,942,179 | A | 8/1999 | Tallentire |
| 5,952,286 | A | 9/1999 | Puvvada et al. |
| 5,955,419 | A | 9/1999 | Barket, Jr. et al. |
| D416,103 | S | 11/1999 | Hashmi |
| 5,976,454 | A | 11/1999 | Sterzel et al. |
| D418,415 | S | 1/2000 | Hayes et al. |
| D418,750 | S | 1/2000 | Blin |
| 6,010,719 | A | 1/2000 | Remon et al. |
| 6,028,016 | A | 2/2000 | Yahiaoui et al. |
| 6,029,808 | A | 2/2000 | Peck et al. |
| 6,034,043 | A | 3/2000 | Fujiwara et al. |
| 6,037,319 | A | 3/2000 | Dickler |
| 6,066,396 | A | 5/2000 | Inada |
| 6,074,997 | A | 6/2000 | Rau et al. |
| 6,080,346 | A | 6/2000 | Jack |
| D427,902 | S | 7/2000 | Hayes et al. |
| 6,106,849 | A | 8/2000 | Malkan et al. |
| 6,130,193 | A | 10/2000 | Gillette |
| 6,175,054 | B1 | 1/2001 | Jacques |
| 6,177,391 | B1 | 1/2001 | Zafar |
| 6,197,238 | B1 | 3/2001 | Wang |
| 6,200,949 | B1 | 3/2001 | Reijmer et al. |
| 6,207,274 | B1 | 3/2001 | Ferenc |
| D441,869 | S | 5/2001 | Bloor et al. |
| D442,353 | S | 5/2001 | Macias |
| D442,739 | S | 5/2001 | Friesenhahn |
| D443,389 | S | 6/2001 | Friesenhahn |
| 6,274,162 | B1 | 8/2001 | Steffenino |
| D448,802 | S | 10/2001 | Lariviere, Jr. et al. |
| D449,881 | S | 10/2001 | Mock, Sr. |
| D450,378 | S | 11/2001 | Minakuchi et al. |
| 6,319,510 | B1 | 11/2001 | Yates |
| 6,335,312 | B1 | 1/2002 | Coffindaffer et al. |
| 6,365,142 | B1 | 4/2002 | Tamura |
| 6,382,526 | B1 | 5/2002 | Reneker et al. |
| 6,406,797 | B1 | 6/2002 | Vanputte |
| 6,417,156 | B1 | 7/2002 | Smith et al. |
| 6,420,625 | B1 | 7/2002 | Jones |
| 6,426,091 | B1 | 7/2002 | Okumura et al. |
| 6,440,926 | B1 | 8/2002 | Spadoni et al. |
| D462,900 | S | 9/2002 | Yamada et al. |
| 6,448,462 | B2 | 9/2002 | Groitzsch |
| 6,458,754 | B1 | 10/2002 | Velazquez et al. |
| 6,465,407 | B2 | 10/2002 | Hayashi |
| D465,303 | S | 11/2002 | Friesenhahn |
| 6,503,521 | B1 | 1/2003 | Atis et al. |
| 6,525,034 | B2 | 2/2003 | Dalrymple et al. |
| 6,552,123 | B1 | 4/2003 | Katayama |
| 6,576,575 | B2 | 6/2003 | Griesbach |
| 6,608,121 | B2 | 8/2003 | Isozaki |
| D479,561 | S | 9/2003 | Meyer |
| 6,623,694 | B1 | 9/2003 | Ferguson et al. |
| 6,657,004 | B2 | 12/2003 | Mizutani |
| D484,749 | S | 1/2004 | Garraway |
| 6,699,826 | B1 | 3/2004 | Saijo |
| 6,723,160 | B2 | 4/2004 | Mackey et al. |
| D489,162 | S | 5/2004 | Dings-plooij |
| 6,730,648 | B2 | 5/2004 | Gorlin |
| 6,783,852 | B2 | 8/2004 | Inada |
| 6,787,512 | B1 | 9/2004 | Verrall |
| 6,790,814 | B1 | 9/2004 | Marin |
| 6,800,295 | B2 | 10/2004 | Fox |
| 6,802,295 | B2 | 10/2004 | Bedwell et al. |
| 6,808,375 | B2 | 10/2004 | Kloetzer |
| 6,808,598 | B1 | 10/2004 | Takeuchi |
| 6,818,606 | B1 | 11/2004 | Hanada |
| 6,825,161 | B2 | 11/2004 | Shefer et al. |
| 6,831,046 | B2 | 12/2004 | Carew et al. |
| 6,846,784 | B2 | 1/2005 | Engel et al. |
| 6,878,368 | B2 | 4/2005 | Ohta et al. |
| 6,898,819 | B2 | 5/2005 | Tanaka et al. |
| 6,898,921 | B2 | 5/2005 | Duffield |
| D509,935 | S | 9/2005 | Burt |
| 6,943,200 | B1 | 9/2005 | Corrand et al. |
| 6,946,506 | B2 | 9/2005 | Bond et al. |
| 6,949,498 | B2 | 9/2005 | Murphy |
| 6,956,070 | B2 | 10/2005 | Fujiwara |
| 6,977,116 | B2 | 12/2005 | Cabell |
| D515,915 | S | 2/2006 | Karim |
| 7,015,181 | B2 | 3/2006 | Lambino |
| 7,026,049 | B2 | 4/2006 | Endo |
| 7,041,369 | B1 | 5/2006 | Mackey et al. |
| 7,067,575 | B2 | 6/2006 | Kitamura |
| 7,083,047 | B2 | 8/2006 | Bone |
| 7,094,744 | B1 | 8/2006 | Kobayashi |
| 7,115,551 | B2 | 10/2006 | Hasenoehrl |
| 7,125,828 | B2 | 10/2006 | Catlin |
| 7,169,740 | B2 | 1/2007 | Sommerville-roberts |
| 7,172,765 | B2 | 2/2007 | Chu et al. |
| 7,196,026 | B2 | 3/2007 | Di Luccio |
| RE39,557 | E | 4/2007 | Moe |
| 7,208,460 | B2 | 4/2007 | Shefer et al. |
| 7,221,900 | B2 | 5/2007 | Reade et al. |
| 7,226,899 | B2 | 6/2007 | Cole |
| D549,051 | S | 8/2007 | Nordwall |
| 7,285,520 | B2 | 10/2007 | Krzysik |
| 7,291,300 | B2 | 11/2007 | Chhabra et al. |
| 7,387,787 | B2 | 6/2008 | Fox |
| 7,407,669 | B2 | 8/2008 | Leung |
| D576,753 | S | 9/2008 | Mukai |
| D577,332 | S | 9/2008 | Moore |
| 7,429,273 | B2 | 9/2008 | De Dominicis |
| D578,881 | S | 10/2008 | Friedland et al. |
| 7,446,084 | B2 | 11/2008 | Barthel |
| 7,491,407 | B2 | 2/2009 | Pourdeyhimi |
| D588,332 | S | 3/2009 | Phelan |
| 7,507,698 | B2 | 3/2009 | Franzolin |
| 7,547,737 | B2 | 6/2009 | Kochvar |
| 7,563,757 | B2 | 7/2009 | Kouvroukoglou |
| 7,704,328 | B2 | 4/2010 | Bailey et al. |
| 7,708,840 | B2 | 5/2010 | Wiedemann |
| 7,727,946 | B2 | 6/2010 | Catalfamo |
| 7,824,588 | B2 | 11/2010 | Yang |
| 7,832,552 | B2 | 11/2010 | Newman |
| 7,846,462 | B2 | 12/2010 | Spadini et al. |
| 7,856,989 | B2 | 12/2010 | Karles |
| 7,892,992 | B2 | 2/2011 | Kamada et al. |
| 7,901,696 | B2 | 3/2011 | Eknoian et al. |
| 7,967,801 | B2 | 6/2011 | Hammons |
| D640,921 | S | 7/2011 | Caldwell |
| D644,541 | S | 9/2011 | Schrader et al. |
| 8,049,061 | B2 | 11/2011 | Ehrenreich et al. |
| D651,096 | S | 12/2011 | Nakagiri |
| 8,197,830 | B2 | 6/2012 | Helfman et al. |
| 8,268,764 | B2 | 9/2012 | Glenn, Jr. et al. |
| 8,273,333 | B2 | 9/2012 | Glenn, Jr. et al. |
| 8,288,332 | B2 | 10/2012 | Fossum et al. |
| 8,309,505 | B2 | 11/2012 | Fossum et al. |
| 8,349,232 | B2 | 1/2013 | Pourdeyhimi |
| 8,349,341 | B2 | 1/2013 | Glenn, Jr. et al. |
| 8,349,786 | B2 | 1/2013 | Glenn, Jr. et al. |
| 8,349,787 | B2 | 1/2013 | Glenn, Jr. et al. |
| 8,357,728 | B2 | 1/2013 | Butler et al. |
| 8,367,596 | B2 | 2/2013 | Fossum et al. |
| D680,882 | S | 4/2013 | Logue |
| 8,415,287 | B2 | 4/2013 | Glenn, Jr. et al. |
| D682,622 | S | 5/2013 | Keys |
| 8,453,653 | B2 | 6/2013 | Mishra et al. |
| 8,461,090 | B2 | 6/2013 | Glenn, Jr. et al. |

(56) References Cited

U.S. PATENT DOCUMENTS

| | | | |
|---|---|---|---|
| 8,461,091 | B2 | 6/2013 | Glenn, Jr. et al. |
| 8,466,099 | B2 | 6/2013 | Glenn, Jr. et al. |
| D685,436 | S | 7/2013 | Menting |
| 8,476,211 | B2 | 7/2013 | Glenn, Jr. et al. |
| 8,541,081 | B1 | 9/2013 | Ranganathan et al. |
| 8,546,640 | B2 | 10/2013 | Popovsky et al. |
| D694,621 | S | 12/2013 | Mccarthy |
| 8,723,333 | B2 | 5/2014 | Park et al. |
| 8,765,170 | B2 | 7/2014 | Glenn, Jr. et al. |
| 8,785,361 | B2 | 7/2014 | Sivik et al. |
| D712,159 | S | 9/2014 | Clerici et al. |
| D712,822 | S | 9/2014 | Brusaw et al. |
| 8,962,501 | B2 | 2/2015 | Johnson et al. |
| 8,980,816 | B2 | 3/2015 | Dreher |
| 9,005,635 | B2 | 4/2015 | Darcy et al. |
| 9,062,186 | B2 | 6/2015 | Longdon et al. |
| 9,074,305 | B2 | 7/2015 | Glenn, Jr. et al. |
| D739,227 | S | 9/2015 | Mitchell et al. |
| 9,125,811 | B2 | 9/2015 | Tojo et al. |
| 9,139,802 | B2 | 9/2015 | Weisman et al. |
| D740,928 | S | 10/2015 | Bruining et al. |
| 9,163,205 | B2 | 10/2015 | Sivik et al. |
| 9,173,826 | B2 | 11/2015 | Schwartz et al. |
| 9,175,250 | B2 | 11/2015 | Sivik et al. |
| 9,198,838 | B2 | 12/2015 | Glenn, Jr. et al. |
| D748,240 | S | 1/2016 | Goode |
| 9,421,153 | B2 | 8/2016 | Sivik et al. |
| D769,522 | S | 10/2016 | Venet |
| D771,788 | S | 11/2016 | Duckwitz |
| 9,480,628 | B2 | 11/2016 | Sivik et al. |
| D774,086 | S | 12/2016 | Montes et al. |
| D775,198 | S | 12/2016 | Montes et al. |
| 9,539,444 | B2 | 1/2017 | Kinoshita et al. |
| 9,545,364 | B2 | 1/2017 | Glenn, Jr. et al. |
| D778,026 | S | 2/2017 | Roetheli |
| D793,025 | S | 8/2017 | Slusarczyk et al. |
| D797,551 | S | 9/2017 | Chatterton et al. |
| D798,143 | S | 9/2017 | Chatterton |
| D808,583 | S | 1/2018 | Zietek |
| 9,902,077 | B2 | 2/2018 | Park et al. |
| D811,922 | S | 3/2018 | Lefave |
| D811,935 | S | 3/2018 | Hughes |
| D819,836 | S | 6/2018 | Noël |
| 10,045,915 | B2 | 8/2018 | Glenn, Jr. et al. |
| D848,102 | S | 5/2019 | Carlson et al. |
| D850,041 | S | 5/2019 | Endle |
| 10,294,586 | B2 | 5/2019 | Sivik et al. |
| D851,344 | S | 6/2019 | Carlson et al. |
| D857,156 | S | 8/2019 | Hani |
| D857,242 | S | 8/2019 | Darrow et al. |
| D857,929 | S | 8/2019 | Darrow et al. |
| D862,020 | S | 10/2019 | Gorrell et al. |
| D863,600 | S | 10/2019 | Chao |
| D864,507 | S | 10/2019 | Stoughton et al. |
| D866,105 | S | 11/2019 | Carlson et al. |
| D866,891 | S | 11/2019 | Carlson et al. |
| D866,892 | S | 11/2019 | Hunt et al. |
| D866,893 | S | 11/2019 | Hunt et al. |
| D867,717 | S | 11/2019 | Chavez |
| D868,159 | S | 11/2019 | Swisher et al. |
| D868,953 | S | 12/2019 | Mckendree |
| 10,569,286 | B2 | 2/2020 | Anderson et al. |
| D878,694 | S | 3/2020 | Carlson et al. |
| 10,646,413 | B2 | 5/2020 | Sivik et al. |
| 10,694,917 | B2 | 6/2020 | Dreher et al. |
| D901,115 | S | 11/2020 | Carlson et al. |
| D903,152 | S | 11/2020 | Chao |
| 10,821,056 | B2 | 11/2020 | Swartz et al. |
| D906,802 | S | 1/2021 | Chi |
| 10,894,005 | B2 | 1/2021 | Sivik et al. |
| D910,434 | S | 2/2021 | Tan et al. |
| D910,457 | S | 2/2021 | Lee |
| D921,166 | S | 6/2021 | Meyers |
| D933,095 | S | 10/2021 | Heiner et al. |
| 11,351,094 | B2 | 6/2022 | Hamersky et al. |
| 11,395,789 | B2 | 7/2022 | Pratt et al. |
| 11,419,808 | B2 | 8/2022 | Hilvert et al. |
| 11,679,066 | B2 | 6/2023 | Song et al. |
| 12,018,232 | B2 | 6/2024 | Macnamara |
| 2001/0037851 | A1 | 11/2001 | Mortellite |
| 2002/0018906 | A1 | 2/2002 | Clark |
| 2002/0044968 | A1 | 4/2002 | Van Lengerich |
| 2002/0064510 | A1 | 5/2002 | Dalrymple et al. |
| 2002/0077264 | A1 | 6/2002 | Roberts et al. |
| 2002/0081732 | A1 | 6/2002 | Bowlin et al. |
| 2002/0081930 | A1 | 6/2002 | Jackson et al. |
| 2002/0098994 | A1 | 7/2002 | Zafar |
| 2002/0099109 | A1 | 7/2002 | Dufton et al. |
| 2002/0161088 | A1 | 10/2002 | Kochvar |
| 2002/0169092 | A1 | 11/2002 | Alexandre et al. |
| 2002/0173213 | A1 | 11/2002 | Chu |
| 2002/0175449 | A1 | 11/2002 | Chu et al. |
| 2002/0176827 | A1 | 11/2002 | Rajaiah |
| 2002/0177621 | A1 | 11/2002 | Hanada et al. |
| 2002/0187181 | A1 | 12/2002 | Godbey et al. |
| 2003/0013369 | A1 | 1/2003 | Soane et al. |
| 2003/0017208 | A1 | 1/2003 | Ignatious |
| 2003/0018242 | A1 | 1/2003 | Hursh et al. |
| 2003/0032573 | A1 | 2/2003 | Tanner et al. |
| 2003/0045441 | A1 | 3/2003 | Hsu et al. |
| 2003/0045446 | A1 | 3/2003 | Dihora |
| 2003/0054966 | A1 | 3/2003 | Bone et al. |
| 2003/0069154 | A1 | 4/2003 | Hsu et al. |
| 2003/0080150 | A1 | 5/2003 | Cowan et al. |
| 2003/0099691 | A1 | 5/2003 | Lydzinski et al. |
| 2003/0099692 | A1 | 5/2003 | Lydzinski et al. |
| 2003/0114332 | A1 | 6/2003 | Ramcharan et al. |
| 2003/0141662 | A1 | 7/2003 | Kost et al. |
| 2003/0166489 | A1 | 9/2003 | Van Asten et al. |
| 2003/0166495 | A1 | 9/2003 | Wang |
| 2003/0180242 | A1 | 9/2003 | Eccard et al. |
| 2003/0185872 | A1 | 10/2003 | Kochinke |
| 2003/0186826 | A1 | 10/2003 | Eccard et al. |
| 2003/0194416 | A1 | 10/2003 | Shefer |
| 2003/0199412 | A1 | 10/2003 | Gupta |
| 2003/0207776 | A1 | 11/2003 | Shefer et al. |
| 2003/0209166 | A1 | 11/2003 | Vanmaele et al. |
| 2003/0215522 | A1 | 11/2003 | Johnson et al. |
| 2003/0216098 | A1 | 11/2003 | Carlyle |
| 2003/0224959 | A1 | 12/2003 | Smith |
| 2003/0232183 | A1 | 12/2003 | Dufton |
| 2004/0029762 | A1 | 2/2004 | Hensley |
| 2004/0032859 | A1 | 2/2004 | Miao |
| 2004/0048759 | A1 | 3/2004 | Ribble et al. |
| 2004/0048771 | A1 | 3/2004 | Mcdermott et al. |
| 2004/0053808 | A1 | 3/2004 | Raehse et al. |
| 2004/0059055 | A1 | 3/2004 | Inada et al. |
| 2004/0071742 | A1 | 4/2004 | Popplewell |
| 2004/0071755 | A1 | 4/2004 | Fox |
| 2004/0082239 | A1 | 4/2004 | Di Luccio et al. |
| 2004/0092635 | A1 | 5/2004 | Kitamura |
| 2004/0108615 | A1 | 6/2004 | Foley |
| 2004/0110656 | A1 | 6/2004 | Casey et al. |
| 2004/0116018 | A1 | 6/2004 | Fenwick et al. |
| 2004/0116539 | A1 | 6/2004 | Biercevicz et al. |
| 2004/0118852 | A1 | 6/2004 | Barmore et al. |
| 2004/0126585 | A1 | 7/2004 | Kerins et al. |
| 2004/0167256 | A1 | 8/2004 | Verrall |
| 2004/0170836 | A1 | 9/2004 | Bond |
| 2004/0175404 | A1 | 9/2004 | Shefer |
| 2004/0180597 | A1 | 9/2004 | Kamada |
| 2004/0202632 | A1 | 10/2004 | Gott et al. |
| 2004/0204543 | A1 | 10/2004 | Yang |
| 2004/0206270 | A1 | 10/2004 | Vanmaele et al. |
| 2004/0242097 | A1 | 12/2004 | Hasenoehrl |
| 2004/0242772 | A1 | 12/2004 | Huth et al. |
| 2004/0253434 | A1 | 12/2004 | Patel |
| 2004/0254086 | A1 | 12/2004 | Hedges et al. |
| 2004/0266300 | A1 | 12/2004 | Isele et al. |
| 2005/0003048 | A1 | 1/2005 | Pearce |
| 2005/0003991 | A1 | 1/2005 | Macquarrie |
| 2005/0008776 | A1 | 1/2005 | Chhabra |
| 2005/0010010 | A1 | 1/2005 | Kitamura |
| 2005/0069575 | A1 | 3/2005 | Fox |

(56) References Cited

U.S. PATENT DOCUMENTS

| | | | |
|---|---|---|---|
| 2005/0118237 | A1 | 6/2005 | Krzysik et al. |
| 2005/0136112 | A1 | 6/2005 | Gonzales |
| 2005/0136772 | A1 | 6/2005 | Chen et al. |
| 2005/0136780 | A1 | 6/2005 | Clark et al. |
| 2005/0137115 | A1 | 6/2005 | Cole et al. |
| 2005/0137272 | A1 | 6/2005 | Gaserod |
| 2005/0159730 | A1 | 7/2005 | Kathrani et al. |
| 2005/0180962 | A1 | 8/2005 | Raz et al. |
| 2005/0186256 | A1 | 8/2005 | Dihel |
| 2005/0202992 | A1 | 9/2005 | Grandio et al. |
| 2005/0209574 | A1 | 9/2005 | Boehringer |
| 2005/0220745 | A1 | 10/2005 | Lu |
| 2005/0232954 | A1 | 10/2005 | Yoshinari et al. |
| 2005/0253297 | A1 | 11/2005 | Pedmo et al. |
| 2005/0267005 | A1 | 12/2005 | Dasque et al. |
| 2005/0272836 | A1 | 12/2005 | Yaginuma et al. |
| 2005/0281757 | A1 | 12/2005 | Ibrahim |
| 2005/0287106 | A1 | 12/2005 | Legendre |
| 2006/0002880 | A1 | 1/2006 | Peffly et al. |
| 2006/0013869 | A1 | 1/2006 | Ignatious |
| 2006/0035042 | A1 | 2/2006 | Morken |
| 2006/0052263 | A1 | 3/2006 | Roreger et al. |
| 2006/0064510 | A1 | 3/2006 | Low et al. |
| 2006/0078528 | A1 | 4/2006 | Yang et al. |
| 2006/0078529 | A1 | 4/2006 | Uchida et al. |
| 2006/0083784 | A1 | 4/2006 | Ignatious |
| 2006/0089276 | A1 | 4/2006 | Klotz |
| 2006/0127458 | A1 | 6/2006 | Kiser |
| 2006/0128592 | A1 | 6/2006 | Ross et al. |
| 2006/0134412 | A1 | 6/2006 | Mackey |
| 2006/0135026 | A1 | 6/2006 | Arendt et al. |
| 2006/0159730 | A1 | 7/2006 | Simon |
| 2006/0160453 | A1 | 7/2006 | Suh |
| 2006/0189772 | A1 | 8/2006 | Scheibel |
| 2006/0228319 | A1 | 10/2006 | Vona, Jr. et al. |
| 2006/0254013 | A1 | 11/2006 | Konishi |
| 2006/0254014 | A1 | 11/2006 | Konishi |
| 2006/0258251 | A1 | 11/2006 | Konishi |
| 2006/0264130 | A1 | 11/2006 | Karles |
| 2006/0274263 | A1 | 12/2006 | Yacktman et al. |
| 2007/0028939 | A1 | 2/2007 | Mareri et al. |
| 2007/0054579 | A1 | 3/2007 | Baker, Jr. |
| 2007/0098749 | A1 | 5/2007 | Eknoian et al. |
| 2007/0099813 | A1 | 5/2007 | Luizzi et al. |
| 2007/0110792 | A9 | 5/2007 | Simon |
| 2007/0128256 | A1 | 6/2007 | Aubrun-sonneville |
| 2007/0134304 | A1 | 6/2007 | Aubrun-sonneville |
| 2007/0134481 | A1 | 6/2007 | Aubrun-sonneville |
| 2007/0135528 | A1 | 6/2007 | Butler et al. |
| 2007/0149435 | A1 | 6/2007 | Koenig et al. |
| 2007/0225388 | A1 | 9/2007 | Cooper et al. |
| 2007/0253926 | A1 | 11/2007 | Tadrowski |
| 2007/0259170 | A1 | 11/2007 | Brown |
| 2007/0259996 | A1 | 11/2007 | Vicari |
| 2007/0269651 | A1 | 11/2007 | Denome et al. |
| 2007/0298064 | A1 | 12/2007 | Koslow |
| 2008/0008906 | A1 | 1/2008 | Catalfamo |
| 2008/0019935 | A1 | 1/2008 | Khan |
| 2008/0035174 | A1 | 2/2008 | Aubrun-Sonneville |
| 2008/0083420 | A1 | 4/2008 | Glenn et al. |
| 2008/0087293 | A1 | 4/2008 | Glenn et al. |
| 2008/0090939 | A1 | 4/2008 | Netravali et al. |
| 2008/0095828 | A1 | 4/2008 | Privitera et al. |
| 2008/0108748 | A1 | 5/2008 | Buckley |
| 2008/0118727 | A1 | 5/2008 | Andersen |
| 2008/0131695 | A1 | 6/2008 | Aouad et al. |
| 2008/0138492 | A1 | 6/2008 | Cingotti |
| 2008/0146481 | A1 | 6/2008 | Brown |
| 2008/0149119 | A1 | 6/2008 | Shen |
| 2008/0152894 | A1 | 6/2008 | Beihoffer et al. |
| 2008/0153730 | A1 | 6/2008 | Tsaur et al. |
| 2008/0215023 | A1 | 9/2008 | Scavone et al. |
| 2008/0220054 | A1 | 9/2008 | Shastri |
| 2008/0226919 | A1 | 9/2008 | Hosoda |
| 2008/0242572 | A1 | 10/2008 | Icht |
| 2008/0269095 | A1 | 10/2008 | Aubrun-sonneville |
| 2008/0276178 | A1 | 11/2008 | Fadell et al. |
| 2008/0279905 | A1 | 11/2008 | Kawamoto et al. |
| 2008/0292669 | A1 | 11/2008 | Deng et al. |
| 2008/0293839 | A1 | 11/2008 | Stobby |
| 2009/0004254 | A1 | 1/2009 | Maibach |
| 2009/0041820 | A1 | 2/2009 | Wu et al. |
| 2009/0054860 | A1 | 2/2009 | Young et al. |
| 2009/0061225 | A1 | 3/2009 | Bailey et al. |
| 2009/0061496 | A1 | 3/2009 | Kuhn |
| 2009/0061719 | A1 | 3/2009 | Shibutani |
| 2009/0144913 | A1 | 6/2009 | Yu et al. |
| 2009/0155326 | A1 | 6/2009 | Mack |
| 2009/0155383 | A1 | 6/2009 | Kitko et al. |
| 2009/0181587 | A1 | 7/2009 | Kang |
| 2009/0197787 | A1 | 8/2009 | Venet et al. |
| 2009/0232873 | A1 | 9/2009 | Glenn, Jr. et al. |
| 2009/0247036 | A1 | 10/2009 | Shi et al. |
| 2009/0249558 | A1 | 10/2009 | Fileccia |
| 2009/0258099 | A1 | 10/2009 | Brown et al. |
| 2009/0263342 | A1 | 10/2009 | Glenn, Jr. et al. |
| 2009/0285718 | A1 | 11/2009 | Privitera |
| 2009/0286437 | A1 | 11/2009 | Cunningham et al. |
| 2009/0291282 | A1 | 11/2009 | Kitamura et al. |
| 2009/0293281 | A1 | 12/2009 | Bruno |
| 2009/0312220 | A1 | 12/2009 | Boutoille |
| 2010/0018641 | A1 | 1/2010 | Branham |
| 2010/0021517 | A1 | 1/2010 | Ahlers |
| 2010/0098745 | A1 | 4/2010 | Staab |
| 2010/0105821 | A1 | 4/2010 | Verrall |
| 2010/0135921 | A1 | 6/2010 | Hughes et al. |
| 2010/0150976 | A1 | 6/2010 | Schnitzler et al. |
| 2010/0166854 | A1 | 7/2010 | Michniak-kohn |
| 2010/0167971 | A1 | 7/2010 | Glenn, Jr. et al. |
| 2010/0173817 | A1 | 7/2010 | Glenn, Jr. et al. |
| 2010/0179083 | A1 | 7/2010 | Glenn, Jr. et al. |
| 2010/0196440 | A1 | 8/2010 | Stark |
| 2010/0266668 | A1 | 10/2010 | Coffee |
| 2010/0279905 | A1 | 11/2010 | Glenn, Jr. |
| 2010/0285101 | A1 | 11/2010 | Moore |
| 2010/0286011 | A1 | 11/2010 | Glenn, Jr. et al. |
| 2010/0291165 | A1 | 11/2010 | Glenn, Jr. et al. |
| 2010/0298188 | A1 | 11/2010 | Glenn, Jr. et al. |
| 2011/0014252 | A1 | 1/2011 | Sagel et al. |
| 2011/0023240 | A1 | 2/2011 | Fossum |
| 2011/0027328 | A1 | 2/2011 | Baig et al. |
| 2011/0028373 | A1 | 2/2011 | Fossum et al. |
| 2011/0028374 | A1 | 2/2011 | Fossum et al. |
| 2011/0033509 | A1 | 2/2011 | Simon |
| 2011/0045041 | A1 | 2/2011 | Golubovic-liakopoulos et al. |
| 2011/0123596 | A1 | 5/2011 | Baecker et al. |
| 2011/0129510 | A1 | 6/2011 | Liebmann |
| 2011/0136719 | A1 | 6/2011 | Jalbert |
| 2011/0159267 | A1 | 6/2011 | Lee |
| 2011/0165110 | A1 | 7/2011 | Kinoshita et al. |
| 2011/0182956 | A1 | 7/2011 | Glenn, Jr. et al. |
| 2011/0189246 | A1 | 8/2011 | Glenn, Jr. et al. |
| 2011/0189247 | A1 | 8/2011 | Glenn, Jr. et al. |
| 2011/0195098 | A1 | 8/2011 | Glenn, Jr. et al. |
| 2011/0223381 | A1 | 9/2011 | Sauter |
| 2011/0230112 | A1 | 9/2011 | Rose |
| 2011/0250256 | A1 | 10/2011 | Hyun-Oh et al. |
| 2011/0287687 | A1 | 11/2011 | Kramer et al. |
| 2011/0301070 | A1 | 12/2011 | Ochomogo |
| 2012/0021026 | A1 | 1/2012 | Glenn, Jr. |
| 2012/0027838 | A1 | 2/2012 | Gordon et al. |
| 2012/0048769 | A1 | 3/2012 | Sivik |
| 2012/0052036 | A1 | 3/2012 | Glenn, Jr. |
| 2012/0052037 | A1 | 3/2012 | Sivik et al. |
| 2012/0053103 | A1 | 3/2012 | Sivik |
| 2012/0053108 | A1 | 3/2012 | Glenn, Jr. |
| 2012/0058100 | A1 | 3/2012 | Shastri et al. |
| 2012/0058166 | A1 | 3/2012 | Glenn, Jr. |
| 2012/0082037 | A1 | 4/2012 | Wang |
| 2012/0107534 | A1 | 5/2012 | Wnuk et al. |
| 2012/0172831 | A1 | 7/2012 | Darcy |
| 2012/0215148 | A1 | 8/2012 | Ewert |
| 2012/0237576 | A1 | 9/2012 | Gordon |
| 2012/0258902 | A1 | 10/2012 | Parrish et al. |

(56) References Cited

U.S. PATENT DOCUMENTS

| | | | |
|---|---|---|---|
| 2012/0270029 | A1 | 10/2012 | Glenn, Jr. et al. |
| 2012/0288693 | A1 | 11/2012 | Stanley et al. |
| 2012/0294823 | A1 | 11/2012 | Aramwit |
| 2012/0321580 | A1 | 12/2012 | Glenn, Jr. |
| 2013/0052277 | A1 | 2/2013 | Weiss et al. |
| 2013/0142852 | A1 | 6/2013 | Tojo et al. |
| 2013/0171421 | A1 | 7/2013 | Weisman |
| 2013/0230482 | A1 | 9/2013 | Saguchi et al. |
| 2013/0236520 | A1 | 9/2013 | Popovsky et al. |
| 2013/0280979 | A1 | 10/2013 | Mckee |
| 2013/0303419 | A1 | 11/2013 | Glenn, Jr. et al. |
| 2014/0017402 | A1 | 1/2014 | Kleinwaechter et al. |
| 2014/0039114 | A1 | 2/2014 | Hagihara et al. |
| 2014/0105946 | A1 | 4/2014 | Glenn, Jr. et al. |
| 2014/0127145 | A1 | 5/2014 | Deckner |
| 2014/0128345 | A1 | 5/2014 | Woodrow et al. |
| 2014/0265007 | A1 | 9/2014 | Bruning et al. |
| 2014/0271744 | A1 | 9/2014 | Glenn, Jr. et al. |
| 2014/0271745 | A1 | 9/2014 | Glenn, Jr. et al. |
| 2014/0287973 | A1 | 9/2014 | Sivik |
| 2014/0329428 | A1 | 11/2014 | Glenn, Jr. et al. |
| 2015/0044157 | A1 | 2/2015 | Kulkarni et al. |
| 2015/0071572 | A1 | 3/2015 | Dreher |
| 2015/0102307 | A1 | 4/2015 | Tajima et al. |
| 2015/0157548 | A1 | 6/2015 | De Feij et al. |
| 2015/0297494 | A1 | 10/2015 | Mao et al. |
| 2015/0313803 | A1 | 11/2015 | Lynch et al. |
| 2015/0313804 | A1 | 11/2015 | Lynch et al. |
| 2015/0313805 | A1 | 11/2015 | Lynch et al. |
| 2015/0313806 | A1 | 11/2015 | Lynch et al. |
| 2015/0313807 | A1 | 11/2015 | Lynch et al. |
| 2015/0313808 | A1 | 11/2015 | Lynch et al. |
| 2015/0313809 | A1 | 11/2015 | Lynch et al. |
| 2015/0315350 | A1 | 11/2015 | Mao et al. |
| 2016/0008235 | A1 | 1/2016 | Sivik et al. |
| 2016/0010041 | A1 | 1/2016 | Sivik et al. |
| 2016/0101026 | A1 | 4/2016 | Pratt et al. |
| 2016/0101204 | A1 | 4/2016 | Lynch et al. |
| 2016/0143827 | A1 | 5/2016 | Castan Barberan et al. |
| 2016/0250109 | A1 | 9/2016 | Dreher et al. |
| 2016/0324741 | A1 | 11/2016 | Baig |
| 2016/0367104 | A1 | 12/2016 | Dreher et al. |
| 2017/0121641 | A1 | 5/2017 | Smith |
| 2017/0319876 | A1 | 11/2017 | Hentrich et al. |
| 2017/0335080 | A1 | 11/2017 | Mao et al. |
| 2018/0015643 | A1 | 1/2018 | Patel et al. |
| 2018/0104177 | A1 | 4/2018 | Constantine et al. |
| 2018/0110710 | A1 | 4/2018 | Zhao et al. |
| 2018/0140469 | A1 | 5/2018 | Kane et al. |
| 2018/0163325 | A1 | 6/2018 | Glenn, Jr. et al. |
| 2018/0258555 | A1 | 9/2018 | Glenn, Jr. |
| 2018/0311135 | A1 | 11/2018 | Chang et al. |
| 2018/0333339 | A1 | 11/2018 | Hamersky |
| 2018/0334644 | A1 | 11/2018 | Hamersky et al. |
| 2018/0338890 | A1 | 11/2018 | Glenn, Jr. |
| 2019/0015875 | A1 | 1/2019 | Gardner, Jr. et al. |
| 2019/0105243 | A1 | 4/2019 | Song et al. |
| 2019/0282457 | A1 | 9/2019 | Pratt et al. |
| 2019/0282461 | A1 | 9/2019 | Glassmeyer et al. |
| 2019/0350819 | A1 | 11/2019 | Hamersky |
| 2020/0071851 | A1 | 3/2020 | Glenn, Jr. et al. |
| 2020/0093710 | A1 | 3/2020 | Hamersky et al. |
| 2020/0214946 | A1 | 7/2020 | Chan et al. |
| 2020/0261326 | A1 | 8/2020 | Sivik et al. |
| 2020/0275818 | A1 | 9/2020 | Dreher et al. |
| 2020/0308360 | A1 | 10/2020 | Mao et al. |
| 2020/0405587 | A1 | 12/2020 | Song |
| 2021/0000733 | A1 | 1/2021 | Hilvert |
| 2021/0094744 | A1 | 4/2021 | Benson et al. |
| 2021/0107263 | A1 | 4/2021 | Bartolucci et al. |
| 2021/0121373 | A1 | 4/2021 | Tan et al. |
| 2021/0128417 | A1 | 5/2021 | Sivik et al. |
| 2021/0137798 | A1 | 5/2021 | Sivik et al. |
| 2021/0147763 | A1 | 5/2021 | Tan et al. |
| 2021/0189602 | A1 | 6/2021 | Glenn, Jr. et al. |
| 2021/0261885 | A1 | 8/2021 | Tibbs et al. |
| 2021/0322290 | A1 | 10/2021 | Lynch et al. |
| 2021/0401677 | A1 | 12/2021 | Song |
| 2022/0054365 | A1 | 2/2022 | Xu et al. |
| 2022/0257476 | A1 | 8/2022 | Hamersky et al. |
| 2022/0323309 | A1 | 10/2022 | Pratt et al. |

FOREIGN PATENT DOCUMENTS

| | | | |
|---|---|---|---|
| CA | 2524099 | A1 | 4/2006 |
| CA | 2695068 | A1 | 9/2010 |
| CA | 166297 | | 5/2018 |
| CA | 169627 | S | 5/2018 |
| CN | 1138091 | | 12/1996 |
| CN | 1219388 | | 6/1999 |
| CN | 1268558 | | 10/2000 |
| CN | 1357613 | A | 7/2002 |
| CN | 1454231 | A | 11/2003 |
| CN | 1530431 | A | 9/2004 |
| CN | 1583991 | A | 2/2005 |
| CN | 1726074 | A | 1/2006 |
| CN | 3648760 | | 5/2007 |
| CN | 101161877 | A | 4/2008 |
| CN | 101280467 | A | 10/2008 |
| CN | 101424009 | A | 5/2009 |
| CN | 101538745 | A | 9/2009 |
| CN | 301666535 | | 9/2011 |
| CN | 103735428 | A | 4/2014 |
| CN | 304115833 | | 4/2017 |
| CN | 106726634 | A | 5/2017 |
| CN | 106728634 | A | 5/2017 |
| CN | 106916659 | A | 7/2017 |
| CN | 304537587 | | 3/2018 |
| DE | 19607851 | A1 | 9/1997 |
| DE | 10331767 | A1 | 2/2005 |
| DE | 102007011606 | A1 | 9/2008 |
| EP | 0392608 | A2 | 10/1990 |
| EP | 609808 | A1 | 8/1994 |
| EP | 0858828 | A1 | 8/1998 |
| EP | 0948960 | A2 | 10/1999 |
| EP | 1048722 | A1 | 11/2000 |
| EP | 1160311 | A2 | 12/2001 |
| EP | 1214879 | A2 | 6/2002 |
| EP | 1227152 | A1 | 7/2002 |
| EP | 1275368 | A1 | 1/2003 |
| EP | 1306425 | A2 | 5/2003 |
| EP | 1217987 | B1 | 12/2004 |
| EP | 1574561 | A1 | 9/2005 |
| EP | 1375377 | B1 | 10/2005 |
| EP | 1614790 | A1 | 1/2006 |
| EP | 1409628 | B1 | 2/2006 |
| EP | 1512701 | B1 | 6/2006 |
| EP | 1887036 | A2 | 2/2008 |
| EP | 1888036 | | 2/2008 |
| EP | 1958532 | A2 | 8/2008 |
| EP | 2085434 | A1 | 8/2009 |
| EP | 1436376 | B1 | 4/2010 |
| EP | 2226379 | A1 | 9/2010 |
| EP | 1317916 | B1 | 10/2010 |
| EP | 2246031 | A1 | 11/2010 |
| EP | 1948771 | B1 | 12/2010 |
| EP | 2319965 | A1 | 5/2011 |
| EP | 2363432 | A1 | 9/2011 |
| EP | 2363517 | A1 | 9/2011 |
| EP | 2395142 | A1 | 12/2011 |
| FR | 2871685 | A1 | 12/2005 |
| FR | 2886845 | A1 | 12/2006 |
| GB | 2107579 | A | 5/1983 |
| GB | 2235204 | A | 2/1991 |
| GB | 2355008 | A | 4/2001 |
| GB | 2375542 | A | 11/2002 |
| GB | 2378407 | A | 2/2003 |
| GB | 2449418 | A | 11/2008 |
| HU | 221299 | B1 | 9/2002 |
| IN | 20150354411 | | 5/2017 |
| JP | S4912158 | A | 2/1974 |
| JP | 58021608 | | 2/1983 |
| JP | S58216109 | A | 12/1983 |
| JP | S59163458 | A | 9/1984 |

(56) References Cited

FOREIGN PATENT DOCUMENTS

| | | | |
|---|---|---|---|
| JP | S6272609 | A | 4/1987 |
| JP | S6272610 | A | 4/1987 |
| JP | S6281432 | A | 4/1987 |
| JP | S6281462 | A | 4/1987 |
| JP | 62156348 | | 7/1987 |
| JP | S6346251 | A | 2/1988 |
| JP | S63156715 | A | 6/1988 |
| JP | H01172319 | A | 7/1989 |
| JP | H01229805 | A | 9/1989 |
| JP | H01313418 | A | 12/1989 |
| JP | H0243268 | A | 2/1990 |
| JP | H0275650 | A | 3/1990 |
| JP | H02280771 | A | 11/1990 |
| JP | 3040879 | A | 2/1991 |
| JP | 3101618 | A | 4/1991 |
| JP | H05344873 | A | 12/1993 |
| JP | H0617083 | A | 1/1994 |
| JP | H06116568 | A | 4/1994 |
| JP | 0753349 | | 2/1995 |
| JP | H0789852 | A | 4/1995 |
| JP | H07173724 | A | 7/1995 |
| JP | H08325133 | A | 12/1996 |
| JP | H09216809 | A | 8/1997 |
| JP | H09216909 | A | 8/1997 |
| JP | 09279457 | | 10/1997 |
| JP | 10008364 | A | 1/1998 |
| JP | H101824 | A | 1/1998 |
| JP | 10158700 | A | 6/1998 |
| JP | H10251371 | A | 9/1998 |
| JP | H10251952 | A | 9/1998 |
| JP | H10512929 | A | 12/1998 |
| JP | H11505569 | A | 5/1999 |
| JP | H11513053 | A | 11/1999 |
| JP | 2000053998 | A | 2/2000 |
| JP | 2000169896 | A | 6/2000 |
| JP | 2000212828 | A | 8/2000 |
| JP | 2000229841 | A | 8/2000 |
| JP | 2001302868 | A | 10/2001 |
| JP | 2001519376 | A | 10/2001 |
| JP | 2002201531 | A | 7/2002 |
| JP | 2002226895 | A | 8/2002 |
| JP | 2003073700 | A | 3/2003 |
| JP | 2003082397 | A | 3/2003 |
| JP | 2003532554 | A | 11/2003 |
| JP | 2004256799 | A | 9/2004 |
| JP | 2004533551 | A | 11/2004 |
| JP | 2004345983 | A | 12/2004 |
| JP | 2005509734 | A | 4/2005 |
| JP | 2005171063 | A | 6/2005 |
| JP | 2005534716 | A | 11/2005 |
| JP | 20060021337 | A | 1/2006 |
| JP | 2006056835 | A | 3/2006 |
| JP | 2006511732 | A | 4/2006 |
| JP | 3828217 | B2 | 7/2006 |
| JP | 2006249029 | A | 9/2006 |
| JP | 2007001889 | A | 1/2007 |
| JP | 2007091954 | A | 4/2007 |
| JP | 2007197365 | A | 8/2007 |
| JP | 2007197540 | A | 8/2007 |
| JP | 2007528748 | A | 10/2007 |
| JP | 2007533763 | A | 11/2007 |
| JP | 4128580 | B2 | 5/2008 |
| JP | 2008156807 | A | 7/2008 |
| JP | 2008525436 | A | 7/2008 |
| JP | 2009079329 | A | 4/2009 |
| JP | 2009533569 | A | 9/2009 |
| JP | 4510221 | B2 | 5/2010 |
| JP | 2010100966 | A | 5/2010 |
| JP | 2010126856 | A | 6/2010 |
| JP | 2013505375 | A | 2/2013 |
| JP | 2013099467 | A | 5/2013 |
| JP | 5344873 | B2 | 8/2013 |
| JP | 2013531145 | A | 8/2013 |
| JP | 2013531748 | A | 8/2013 |
| JP | 2015509147 | A | 3/2015 |
| JP | 5821609 | B2 | 10/2015 |
| JP | 2016013984 | A | 1/2016 |
| JP | 6272610 | B2 | 1/2018 |
| KR | 20020003442 | A | 1/2002 |
| KR | 20040094520 | A | 11/2004 |
| RU | 19735 | U1 | 10/2001 |
| RU | 2192451 | C2 | 11/2002 |
| RU | 2300196 | C2 | 6/2007 |
| RU | 2347557 | C2 | 2/2009 |
| TW | 232027 | B | 10/1994 |
| WO | 8301943 | A1 | 6/1983 |
| WO | 1992006603 | A1 | 4/1992 |
| WO | 1994002377 | A1 | 2/1994 |
| WO | 9404656 | A2 | 3/1994 |
| WO | 9514495 | A1 | 6/1995 |
| WO | 9523888 | A1 | 9/1995 |
| WO | 9918182 | A1 | 4/1999 |
| WO | 9951715 | A1 | 10/1999 |
| WO | 9957155 | A1 | 11/1999 |
| WO | 2000013680 | A2 | 3/2000 |
| WO | 0042992 | A2 | 7/2000 |
| WO | 0107194 | A1 | 2/2001 |
| WO | 0110421 | A1 | 2/2001 |
| WO | 0119948 | A1 | 3/2001 |
| WO | 0125322 | A1 | 4/2001 |
| WO | 0125393 | A1 | 4/2001 |
| WO | 200125322 | A1 | 4/2001 |
| WO | 2001024770 | A1 | 4/2001 |
| WO | 200154667 | A1 | 8/2001 |
| WO | 2001054667 | A1 | 8/2001 |
| WO | 0183657 | A2 | 11/2001 |
| WO | 0238722 | A2 | 5/2002 |
| WO | 03044153 | A1 | 5/2003 |
| WO | 03060007 | A1 | 7/2003 |
| WO | 2004009335 | A1 | 1/2004 |
| WO | 2004032859 | A2 | 4/2004 |
| WO | 2004041991 | A1 | 5/2004 |
| WO | 2004081162 | A1 | 9/2004 |
| WO | 2005003423 | A1 | 1/2005 |
| WO | 2005068604 | A1 | 7/2005 |
| WO | 2005070374 | A1 | 8/2005 |
| WO | 2005075547 | A1 | 8/2005 |
| WO | 2006106514 | A2 | 10/2006 |
| WO | 2006130647 | A1 | 12/2006 |
| WO | 2007022229 | A1 | 2/2007 |
| WO | 2007033598 | A1 | 3/2007 |
| WO | 2007089259 | A1 | 8/2007 |
| WO | 2007093558 | A1 | 8/2007 |
| WO | 2007093619 | A1 | 8/2007 |
| WO | 2007102119 | A1 | 9/2007 |
| WO | 2008015641 | A2 | 2/2008 |
| WO | 2008049242 | A1 | 5/2008 |
| WO | 2008104954 | A2 | 9/2008 |
| WO | 2008149248 | A2 | 12/2008 |
| WO | 2009019571 | A2 | 2/2009 |
| WO | 2009022761 | A1 | 2/2009 |
| WO | 2007014221 | A3 | 4/2009 |
| WO | 2009095891 | A1 | 8/2009 |
| WO | 2009103576 | A1 | 8/2009 |
| WO | 2009121900 | A1 | 10/2009 |
| WO | 2010006708 | A1 | 1/2010 |
| WO | 2010015709 | A2 | 2/2010 |
| WO | 2010077627 | A2 | 7/2010 |
| WO | 2010085569 | A1 | 7/2010 |
| WO | 2011153023 | A1 | 12/2011 |
| WO | 2012003349 | A2 | 1/2012 |
| WO | 2012120199 | A1 | 9/2012 |
| WO | 2014158472 | A1 | 10/2014 |
| WO | 2015034975 | A1 | 3/2015 |
| WO | 2015153185 | A1 | 10/2015 |
| WO | DM100932 | | 4/2018 |
| WO | DM100938 | | 4/2018 |
| WO | DM101063 | | 5/2018 |
| WO | DM101100 | | 5/2018 |
| WO | DM101101 | | 5/2018 |
| WO | WO-2018109200 | A1 * | 6/2018 ............ B32B 23/08 |
| WO | 2018140675 | A1 | 8/2018 |

(56) References Cited

FOREIGN PATENT DOCUMENTS

WO 2019001940 A1 1/2019
WO 2020192519 A1 10/2020

OTHER PUBLICATIONS

Pattama Taepaiboon, et al., "Effect of Cross-linking on Properties and ReleaseCharacteristics of Sodium Salicylate-loaded Electrospun Poly (Vinyl Alcohol) FibreMats", Nanotechnology, vol. 18, No. 17, Apr. 2, 2007.
Wikipedia "Polyvinyl alcohol," URL Link—https://en.wikipedia.org/wiki/Polyvinyl_alcohol, dated May 25, 2017, 5 pgs.
"Green Chemistry", Huazhong University of Science and Technology Press, published on Jun. 30, 2008, pp. 6.
Adhesives Research (Pennsylvania, http://12.4.33.51/news/apresmed.htm) (No Known Date).
Afifi-Effat et al., Polymer Letters, 9: 651-655 (1971).
All Office Actions; U.S. Appl. No. 13/173,639, filed Jun. 30, 2011.
All Office Actions; U.S. Appl. No. 13/229,825, filed Sep. 12, 2011.
All Office Actions; U.S. Appl. No. 14/334,862, filed Jul. 18, 2014.
All Office Actions; U.S. Appl. No. 15/170,125, filed Jun. 1, 2016.
All Office Actions; U.S. Appl. No. 15/374,486, filed Dec. 9, 2016.
All Office Actions; U.S. Appl. No. 15/978,503, filed May 14, 2018.
All Office Actions; U.S. Appl. No. 16/674,837, filed Nov. 5, 2019.
All Office Actions; U.S. Appl. No. 17/184,712, filed Feb. 25, 2021.
Amerilab Technologies, Inc. (Minnesota, http://www.amerilabtech.com/) (No Known Date).
Anonymous "P8136 Poly(vinyl alcohol)" Internet article, [Online] XP002538935, Retrieved from the Internet: URL:hllp/20 NWW.sigmaaldrich.com/catalog/ProductDetail.do?D7=0%N25-SEARCH_CONCAT PNOIBRAND KEY%N4=P8136%7SCIAL%N25=0%QS=ON%F=SPEC retrieved on Jul. 28, 2009, year 2009, 1 pg.
Ashland, Klucel hydroxypropylcelllose, accessed at http://www.ashland.com/Ashland/Static/Documents/ASI/ PC_11229_Klucel_HPC.pdf on Apr. 20, 2016.
Briscoe et al. "The effects of hydrogen bonding upon the viscosity of aqueous poly( vinyl alcohol) solutions," from Polymer, 41 (2000), pp. 3851-3860.
Cardinal Health (Dublin, Ohio, http://spd.cardinal.com/) (No Known Date).
Cima Labs, Inc. (Minnesota, http://www.cimalabs.com/) (No Known Date).
Color Keeper [online], [site visited Oct. 18, 2021]. Available from internet, URL: https://shopgemz.com/products/color-keeper?variant=13094595002434&utm_source=google&utm_medium=cpc&utm_campaign=Shopping&gclid=Cj0KCQjw5JSLBhCxARIsAHgO2SdAT7LTehpyxM1qTGtnFETDalNuo9_cQSOpPwCmsmmdGA1Y0USekQEaAh0iEALw_wcB (Year: 2021).
Dahiya, A., Karnath, M.G., Hegde, R.R. Melt Blown Technology, Updated Apr. 2004, downloaded from the sitehttp://www.engr.utk.edu/mse/Textiles/Melt%20Blown%20Technology.htm on Dec. 12, 2015.
Definition of Derivative by Merriam Webster Online Dictionary, Year, 2021, 1 Page.
Design of "Detergent tablets" (Design Registration No. 000634142-0003), (No. of Publicly known information: HH18274488), Registered Community Designs Bulletin, published by EUIPO on Jan. 9, 2007, 4 pgs.
Design of "Detergent tablets" (Design Registration No. 000634142-0004), (No. of Publicly known information: HH18274489), Registered Community Designs Bulletin, published by EUIPO on Jan. 9, 2007, 4 pgs.
Design of "Soaps" accepted on Jul. 11, 1986, Publishing Office: Korean Intellectual Property Office (KIPO), Document Name: Design Gazette (Application No. 3019850005996), Publication Date: Jun. 9, 1986, (No. of Publicly known information: HG21900612), 3 pgs.
Dissolving Soap Strips (Ranir LLC, Michigan, www.ranir.com) (No Known Date).
Dow, UCARE™ Polymer LR-400, Technical Data Sheet, Downloaded in Mar. 2022, 4 pages.
Encyclopedia of Polymer Science and Engineering, vol. 15, 2nd ed., pp. 204 308 Silicones, year 1989.
Francis Ignatious, Linghong Sun, Chao-Pin Lee, and John Baldoni. Electrospun Nanofibers in Oral Drug Delivery—ExpertReview. Pharmaceutical Research, vol. 27, No. 4, Apr. 2010, pp. 576-588. Published online Feb. 9, 2010.
Gemz Hair Care. Perfect Pairs. Publication date unavailable. Visited Jan. 26, 2022. https://shopgemz.com/collections/perfect-pairs (Year: 0).
Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.
Hexagon 4 ward soap mold, Soap, Cosmetics, NEW Silicon mold, Published on Sep. 29, 2016, Retrieved from Internet : http://candle-box.com/product/%EC%9C%A1%EA%B0%81-4%EA%B5%AC-%EB%B9%84%EB%88%84%EB%AA%B0 %EB%93%9C/2206/?page_4=3#none, dated Sep. 10, 2019, 16 pgs.
Hildebrand, T., et al. "Quantification of bone microarchitecture with the structure mode index", Computer Methods in Biomechanics and Biomedical Engineering, vol. 1, Jan. 14, 1997, pp. 15-23.
Hiroshi Yagi & 4 Others, Research Study of a Friction Protector for Preventing a Tow Line From Breaking, Working Papers for Fiscal 2006 I Japan I Japan Coast Guard Idecember 2007, pp. 1-8.
How Gemz work?, Gemz Hair Care, published on Oct. 1, 2018, retrieved on Apr. 27, 2021, retrieved from the Internet URL: https://www.youtube.com/watch?v=ts1waYk43g4, 3 pgs.
Japanese Paper Soap (http://www.wishingfish.com/papersoap.html) (No Known Date).
Karen Duis et al., "Environmental fate and effects of water-soluble synthetic organic polymers used in cosmetic products", Environmental Sciences Europe, vol. 33, Article No. 21, Feb. 16, 2021, 78 pages.
Kuraray: "Mowiol-Technical data sheet", Jun. 1, 2010 (Jun. 1, 2010), Retrieved from the Internet: URL:http://www.kuraray.eu/fileadmin/Downloads/mowiol/TDS_Mowiol_en_20110624.pdf [retrieved on May 23, 2014].
Latorre Carmen, Nanotribological Effects of Hair Careproducts and Environment on Human Hair Using Atomic Forcemicroscopy, Journal of Vacuum Science and Technology: Part A, U.S.A, AVS/AIP , Jun. 28, 2005 , V2 3 N 4, p. 1034-1045.
Le Laboratoire du Bain (France, http://www.laboudubain.com/) (No known date).
L'Alimentation article, Dizolve Group Corporation, Nov. 2010, p. 28.
M.K. Industries (Gujarat India, http://www.soapstrips.com) (No known date).
Makadia, et al., "Poly Lactic-co-Glycolic Acid (PLGA) as Biodegradable ControlledDrug Delivery Carrier", Polymers, 3, pp. 1377-1397 (2011).
Meguiars Car Wash Strips: Meguiars Inc. California, http://www.automotivedigest.com/view_art.asp?articlesID=12414 (No known date).
Ménard et al., "Gnotobiotic Mouse Immune Response Induced by *Bifidobacterium* sp. Strains Isolated from Infants", Applied and Environmental Microbiology, vol. 74, Issue 3, Feb. 1, 2008, pp. 660-666.
Michelle Villett, Why You Need a Sulfate-Free Shampoo, The Skincare Edit, updated date: Jan. 25, 2019, Original publication date: Feb. 22, 2016 (Year: 2016), 7 pages. Mar. 23, 2021.
Minifibers, Inc., accessed on line at http://www.minifibers.com/documents/Choosing-the-Proper-Short-Cut-Fiber.pdf Oct. 3, 2016.
MOVA Pharmaceutical and Kosmos (USA, http://www.icon-pr.com/news/news/prinl.cfm?inv_id=256-1) (No known date).
Ni Genshan et al. "Drug Classification and Pharmacology Summary", PLA Press, published on Apr. 30, 1988, pp. 3.
Okasaka et al., "Evaluation of Anionic Surfactants Effects on the Skin Barrier Function Based on Skin Permeability", Pharmaceutical Development and Technology, vol. 24, No. 1, Jan. 23, 2018, pp. 99-104.
Overview of pharmaceutical excipients used in tablets and capsules in Drug Topics, dated Oct. 24, 2008. Downloaded Sep. 20, 2016

(56) References Cited

OTHER PUBLICATIONS from http://drugtopics.modernmedicine.com/drugtopics/news/modernmedicine/modernmedicinenews/overviewpharmaceuticalexcipientsusedtablets.

Paper Pieces Hexagons, announced 2018 [online], [site visited Oct. 14, 2021]. Available from internet, URL:https://www.amazon.com/Paper-Pieces-HEX100B-Hexagons-1200pc/dp/B07DVYV2HN/ (Year: 2018).

Product Review: Gemz Solid Shampoo, Travel as Much, published on Mar. 19, 2019, retrieved on Apr. 27, 2021, retrieved from the Internet URL: https://travelasmuch.com/gemz-solid-shampoo-review/, 14 pgs.

Pure Soap Leafz: (Soap UNLTD. Netherlands, http://www.upandunder.com.uk/eshop/catalogue/testbs.asp? Manufacturer_ID=252Activity_ID=33Description_ID=157) (No known date).

Raymond C Rowe et al., Polyvinyl Alcohol, Handbook of Pharmaceutical Excipients, 2009, Sixth Edition, Pharmaceutical Press, 564-565.

Retrieved from: https ://www.craftcuts.com/hexagon-craft-shape.html Hexagon wood cutouts, www.craftcuts.com, 1 page, reviewed as early as May 2018 (Year: 2018), 16 pgs.

Rounded hexagon shape, announced 2016 [online], [site visited Oct. 20, 2021], Available from internet, URL:https://www.vexels.com/png-svg/preview/139199/rounded-hexagon-shape (Year: 2016).

Sahin et al. "A Study on Physical and Chemical Properties of Cellulose Paper Immersed in Various Solvent Mixtures" International Journal of Molecular Sciences, Jan. 2008; 9(1): 78-88.

Sanipro Sanitary Products (Italy, http://www.sanipro.iit) (No known date).

Smith, et al., "Nanofibrous Scaffolds and Their Biological Effects", Nantechnologiesfor the Life Sciences, vol. 9, pp. 188-215 (2006).

Solublon (Toyohashi Japan, http://www.solublon.com) (No known date).

SPI Pharma (Delaware, http://www.spipharma.com) (No known date).

Travelers Passport Paper Soap Sheets (http://www.weddingflavornow.com/index.asp?PageAction=VIEWPROD&ProdID=510) (No known date).

Vaughan, C.D. "Solubility, Effects in Product, Package, Penetration and Preservation", Cosmetics and Toiletries, vol. 103, Oct. 1988, 24 pgs.

Vesterby, A.: "Star vol. in Bone Research: A Histomorphometric Analysis of Trabecular Bone Structure Using Vertical Sections", Anal Rec: Feb. 1993, 232(2), pp. 325-334.

W S Ratnayake and D S Jackson. Gelatinization and solubility of corn starch during heating in excess water. Facultyu Publications in Food Science and Technology, Jan. 1, 2006. Also published in Journal of Agricultural and Food Chemistry 54:1 O(2006), pp. 3712-3716.

Wang, et al., "A Novel Controlled Release Drug Delivery System for Multiple DrugsBased on Electrospun Nanofibers Containing Nanoparticles", Journal ofPharmaceutical Sciences, vol. 99, No. 12 (Dec. 2010).

Wenda (China, http://www.wenda.com) (No known date).

Wermuth et al. Drug Discovery, "Drug Discovery Today, 2006", vol. 11 7/8, 348-354, Year 2006.

Yasuhiro Hiramatsu et al. "Bifidobacterium Components Have Immunomodulatory Characteristics Dependent on the Method of Preparation" Cytotechnology, Kluwer Academic Publishers, Do, vol. 55, Issue No. 2-3, Nov. 1, 2007, p. 79-87.

Zhang et al. "Study on Morphology of Electrospun Poly( vinyl alcohol) Mats, " European Polymer Journal 41 (2005), pp. 423-432.

AA01497M PCT Search Report and Written Opinion for PCT/US2022/081495 dated May 12, 2023, 13 pages.

Da Rosa Zavareze, E. et al., Impact of heat-moisture treatment and annealing in starches: A review, Carbohydrate 1 polymers, 83(2), 2011, pp. 317-328.

Database GNPD Mintel, "Dishes & Hands Camp Soap Sheets", XP093208089, Database accession No. 1636025, dated Oct. 6, 2011, 02 Pages.

Database GNPD Mintel, "Soap Leaves", XP093208087, Database accession No. 5336785, dated Dec. 21, 2017, 02 Pages.

* cited by examiner

DISSOLVABLE SOLID FIBROUS SHAMPOO ARTICLES CONTAINING SALTS

FIELD OF THE INVENTION

The present invention relates to a dissolvable solid fibrous shampoo article comprising a plurality of fibrous elements, comprising: a) from about 1% to about 50%, by weight on a dry article basis, of a polymeric structurant; b) from about 0.1.% to about 5% by weight on a dry article basis, of a cationic polymer; c) from about 20% to about 70%, by weight on a dry article basis, of a surfactant; d) from about 5.5% to about 20%, by weight on a dry article basis, of a salt comprising an inorganic salt and an organic salt, wherein the inorganic salt is contained at a level of from about 0% to less than 5% (excluding 5%) by weight on a dry article basis, and wherein the organic salt is contained at a level of from about 1% to about 18% by weight on a dry article basis; wherein the plurality of fibrous elements are intertangled or otherwise associated with one another to form the fibrous article. The present invention provides a dissolvable solid fibrous shampoo articles having an adequate strength during manufacturing while not slowing down the dissolution of the structure during usage.

BACKGROUND OF THE INVENTION

Many personal care and other consumer products in the market today are sold in liquid form. While widely used, liquid products often have tradeoffs in terms of packaging, storage, transportation, and convenience of use. Liquid consumer products typically are sold in bottles which add cost as well as packaging waste, much of which ends up in land-fills.

Hair Care products in the form of a dissolvable solid structures present an attractive form to consumers. Market executions of dissolvable solid structures may include, dissolvable films, compressed powders in a solid, fibrous structures, porous foams, soluble deformable solids, powders, etc.

For example, PCT Patent Application Publication No. WO2020264574A1 discloses a dissolvable solid fibrous shampoo article comprising fibrous elements comprising: (a) from about 1% to about 50%, by weight on a dry article basis of a polymeric structurant; (b) from about 10% to about 90%, by weight on a dry article basis, of a surfactant system wherein the surfactant system is substantially free of sulfate-based surfactants; (c) optionally a cationic polymer comprising a weight average molecular weight from about 100,000 g/mol to about 2.5 million g/mol as measured by gel permeation chromatography and a charge density of greater than 0.5 meg/g as measured according to the Charge Density Test Method; wherein the fibrous article is substantially free of a lamellar structure as determined by the Lamellar Structure Test Method; wherein the fibrous article comprises a hand dissolution of less than 15 strokes according to the Hand Dissolution Test Method.

However, a need still exists for such dissolvable solid structures, especially for those containing cationic polymers, to have an adequate strength during manufacturing while not slowing down the dissolution of the structure during usage.

SUMMARY OF THE INVENTION

The present invention is directed to a dissolvable solid fibrous shampoo article comprising a plurality of fibrous elements, comprising: a) from about 1% to about 50%, by weight on a dry article basis, of a polymeric structurant; b) from about 0.1.% to about 5% by weight on a dry article basis, of a cationic polymer; c) from about 20% to about 70%, by weight on a dry article basis, of a surfactant; d) from about 5.5% to about 20%, by weight on a dry article basis, of a salt comprising an inorganic salt and an organic salt, wherein the inorganic salt is contained at a level of from about 0% to less than 5% (excluding 5%) by weight on a dry article basis, and wherein the organic salt is contained at a level of from about 1% to about 18% by weight on a dry article basis; wherein the plurality of fibrous elements are intertangled or otherwise associated with one another to form the fibrous article. The present invention provides a dissolvable solid fibrous shampoo articles having an adequate strength during manufacturing while not slowing down the dissolution of the structure during usage.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Definitions

As used herein, "dissolvable" means that the Dissolvable Solid Structure is completely soluble in water or it provides a uniform dispersion upon mixing in water according to the hand dissolution test. The Dissolvable Solid Structure has a hand dissolution value of from about 1 to about 20 strokes, and alternatively from about 4 to about 15 strokes, as measured by the Hand Dissolution Method.

As used herein, "flexible" means a Dissolvable Solid Structure meets the distance to maximum force values discussed herein.

"Fibrous article", which is also expressed as "Fibrous structure" interchangeably, as used herein means a structure that comprises one or more fibrous elements and optionally, one or more particles and/or coatings. In one example, a fibrous article according to the present invention means an association of fibrous elements and optionally, particles and/or coatings that together form a structure, such as a unitary structure, capable of performing a function.

Figure 3:
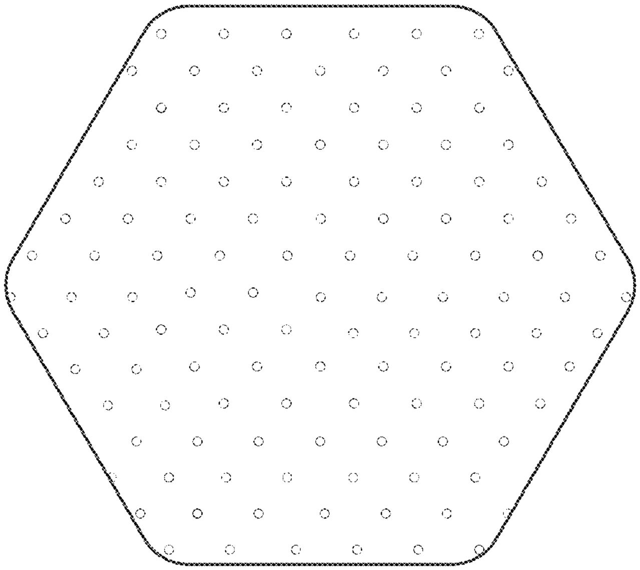
FIG. 3 is an example of a fibrous article containing filaments.

FIG. 3 is an example of a fibrous article containing filaments.

The fibrous articles may be homogeneous or may be layered. If layered, the fibrous articles may comprise at least two and/or at least three and/or at least four and/or at least five layers, for example one or more fibrous element layers, one or more particle layers and/or one or more fibrous element/particle mixture layers. A layer may comprise a particle layer within the fibrous article or between fibrous element layers within a fibrous article. A layer comprising fibrous elements may sometimes be referred to as a ply. A ply may be a fibrous article which may be homogeneous or layered as described herein.

The fibrous structure may have a multi-ply fibrous structure which comprises two or more different fibrous structure plies. Each ply may be the same as or different from other ply.

A layer comprising fibrous elements may sometimes be referred to as a ply. A ply may be a fibrous structure which may be homogeneous or layered as described herein.

The single-ply fibrous structure or a multi-ply fibrous structure comprising one or more fibrous structure plies as described herein may exhibit a basis weight of less than 5000 $g/m^2$ as measured according to the Basis Weight Test Method described herein. For example, the single- or multi-ply fibrous structure according to the present invention may exhibit a basis weight of greater than 10 $g/m^2$ to about 5000 $g/m^2$ and/or greater than 10 $g/m^2$ to about 3000 $g/m^2$ and/or greater than 10 $g/m^2$ to about 2000 $g/m^2$ and/or greater than 10 $g/m^2$ to about 1000 $g/m^2$ and/or greater than 20 $g/m^2$ to about 800 $g/m^2$ and/or greater than 30 $g/m^2$ to about 600 $g/m^2$ and/or greater than 50 $g/m^2$ to about 500 $g/m^2$ and/or greater than 300 $g/m^2$ to about 3000 $g/m^2$ and/or greater than 500 $g/m^2$ to about 2000 $g/m^2$ as measured according to the Basis Weight Test Method.

In one example, the fibrous structure is a "unitary fibrous structure."

"Unitary fibrous structure" as used herein is an arrangement comprising a plurality of two or more and/or three or more fibrous elements that are inter-entangled or otherwise associated with one another to form a fibrous structure and/or fibrous structure plies. A unitary fibrous structure may be one or more plies within a multi-ply fibrous structure. In one example, a unitary fibrous structure may comprise three or more different fibrous elements. In another example, a unitary fibrous structure may comprise two or more different fibrous elements.

"Fibrous element" as used herein means an elongated particulate having a length greatly exceeding its average diameter, i.e., a length to average diameter ratio of at least about 10. A fibrous element may be a filament or a fiber. In one example, the fibrous element is a single fibrous element rather than a yarn comprising a plurality of fibrous elements.

The fibrous elements may be spun from a filament-forming composition also referred to as fibrous element-forming compositions via suitable spinning process operations, such as meltblowing, spunbonding, electro-spinning, and/or rotary spinning.

The fibrous elements may be monocomponent (single, unitary solid piece rather than two different parts, like a core/sheath bicomponent) and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongated particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.). Filaments are typically considered continuous or substantially continuous in nature. Filaments are relatively longer than fibers. Non-limiting examples of filaments include meltblown and/or spunbond filaments.

"Fiber" as used herein means an elongated particulate as described above that exhibits a length of less than 5.08 cm (2 in.) and/or less than 3.81 cm (1.5 in.) and/or less than 2.54 cm (1 in.). Fibers are typically considered discontinuous in nature. Non-limiting examples of fibers include staple fibers produced by spinning a filament or filament tow and then cutting the filament or filament tow into segments of less than 5.08 cm (2 in.) thus producing fibers. Therefore, references to filaments herein also include fibers made from such filaments unless otherwise noted. Fibers are typically considered discontinuous in nature relative to filaments, which are considered continuous in nature.

"Filament-forming composition" and/or "fibrous element-forming composition" as used herein means a composition that is suitable for making a fibrous element such as by meltblowing and/or spunbonding. The filament-forming composition comprises one or more filament-forming materials that exhibit properties that make them suitable for spinning into a fibrous element. In one example, the filament-forming material comprises a polymer. In addition to one or more filament-forming materials, the filament-forming composition may comprise one or more additives, for example one or more active agents. In addition, the filament-forming composition may comprise one or more polar solvents, such as water, into which one or more, for example all, of the filament-forming materials and/or one or more, for example all, of the active agents are dissolved and/or dispersed prior to spinning a fibrous element, such as a filament from the filament-forming composition.

As used herein, "porous" means that the Dissolvable Solid Structure has spaces, voids or interstices, (generally referred to herein as "pores") provided by the microscopic complex three-dimensional configuration, that provide channels, paths or passages through which a liquid can flow.

As used herein, "porosity" and "percent porosity" are used interchangeably and each refers to a measure of void volume of the Dissolvable Solid Structure and is calculated as $$[1-([\text{basis weight of Dissolvable Solid Structure}]/[\text{thickness of Dissolvable Solid Structure}\times\text{density of the bulk, dried material}])]\times100\%$$

with the units adjusted so they cancel and multiplied by 100% to provide percent porosity.

The Dissolvable Solid Structure may be referred to herein as "the Dissolvable Solid Structure" or "the Dissolvable Structure".

"By weight on a dry fibrous element basis" and/or "by weight on a dry fibrous article basis" means the weight of the fibrous element and/or particle and/or fibrous article, respectively, measured immediately after the fibrous element and/or particle and/or fibrous article, respectively, has been conditioned in a conditioned room at a temperature of 22° C.±2° C. and a relative humidity of 42%±4% for 2 hours. In one example, by weight on a dry fibrous element basis and/or dry fibrous article basis means that the fibrous element and/or particle and/or fibrous article comprises less than 20% and/or less than 15% and/or less than 10% and/or less than 7% and/or less than 5% and/or less than 3% and/or to 0% and/or to greater than 0% based on the dry weight of the fibrous element and/or particle and/or fibrous article of moisture, such as water, for example free water, as measured according to the Water Content Test Method described herein.

The term "molecular weight" or "Molecular weight" refers to the weight average molecular weight unless otherwise stated. Molecular weight is measured using industry standard method, gel permeation chromatography ("GPC").

As used herein, the articles including "a" and "an" when used in a claim, are understood to mean one or more of what is claimed or described.

As used herein, the terms "include," "includes," and "including," are meant to be non-limiting.

The methods disclosed in the Test Methods Section of the present application should be used to determine the respective values of the parameters of Applicants' inventions, including those discussed in the Dissolvable Structures—Physical Characteristics section below.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise noted, all component or composition levels are in reference to the active level of that component or composition, and are exclusive of impurities, for example, residual solvents or by-products, which may be present in commercially available sources.

Dissolvable Solid Fibrous Article (Dissolvable Solid Fibrous Structure)

The dissolvable solid fibrous shampoo article may comprise a plurality of fibrous elements, wherein the plurality of fibrous elements is intertangled or otherwise associated with one another to form the fibrous article. Examples of fibrous elements can be found at U.S. patent application Ser. No. 16/431,115, incorporated by reference.

The article can also comprise: polymeric structurant; a cationic polymer; a surfactant; and a salt comprising an inorganic salt and an organic salt. These ingredients are explained below in detail. The fibrous elements can be formed by a homogeneous mixture comprising: polymeric structurant; a cationic polymer; a surfactant; and a salt comprising an inorganic salt and an organic salt. Alternatively, the salt can be incorporated into incorporated into the article outside of fibrous elements, by adding as particles after fibers elements are formed.

The dissolvable solid structure may contain particulates. The dissolvable solid structure may have an aesthetic feature selected from the group consisting of printing, embossing, texture, colored and mixtures thereof.

Salts

The article comprises from about 5.5% to about 20%, by weight on a dry article basis, of a salt comprising an inorganic salt and an organic salt, alternatively from about 7% to about 18%, and alternatively from about 8% to about 16%.

Organic Salt

The organic salt is contained at a level of from about 1% to about 18%, alternatively from about 2% to about 16%, alternatively from about 3% to about 14%, alternatively from about 5.2% to about 14% by weight on a dry article basis.

The organic salts can be salts of organic acids having an average molecular weight (in acid form) of from about 80 to about 400 daltons, alternatively from about 80 to about 200 daltons, alternatively from about 90 to about 150 daltons. Such organic salts include, for example: salts of lactic acids such as sodium lactate and potassium lactate; sodium or potassium salts of citric acid, oxalic acid, malonic acid, tartronic acid, fumaric acid, maleic acid, malic acid, and tartaric acid, and combinations thereof. Non-limiting examples of salts of lactic acids can include sodium lactate and potassium lactate.

Inorganic Salt

The inorganic salt is contained at a level of from about 0% to less than 5% (excluding 5%), alternatively from about 1.2% to about 4.9%, alternatively from about 1.5% to about 4.8% by weight on a dry article basis.

Polymeric Structurant

The melt composition, and/or dissolvable fibrous article and/or fibrous elements can contain from about 1% to 90%, alternatively 10% to about 80%, alternatively from about 20% to about 70%, alternatively from about 30% to about 65%, alternatively from about 35% to about 60%, alternatively from about 20% to about 40%, of a polymeric structurant by weight on a dry fibrous element basis and/or a dry dissolvable fibrous article basis.

Non-limiting examples of fibrous-element forming polymeric structurant materials include water-soluble polymers. The water-soluble polymers may be synthetic or natural original and may be chemically and/or physically modified. The polar solvent-soluble polymers may exhibit a weight average molecular weight of from about 10,000 g/mol to about 40,000,000 g/mol, alternatively from about 20,000 g/mol to about 30,000,000 g/mol, alternatively from about 35,000 g/mol to about 20,000,000 g/mol, even alternatively from about 40,000 g/mol to about 5,000,000 g/mol, most alternatively from about 40,000 g/mol to about 500,000 g/mol.

The one or more fibrous-element forming polymeric structurants comprise one or more polyvinyl alcohols. The one or more polyvinyl alcohols may exhibit a weight average molecular weight of from about 10,000 g/mol to about 40,000,000 g/mol, alternatively from about 20,000 g/mol to about 30,000,000 g/mol, alternatively from about 35,000 g/mol to about 20,000,000 g/mol, alternatively from about 40,000 g/mol to about 5,000,000 g/mol, alternatively from about 40,000 g/mol to about 500,000 g/mol.

The one or more fibrous-element forming polymeric structurant materials may comprise two or more polyvinyl alcohols. One of the two or more polyvinyl alcohols may exhibit a weight average molecular weight of from about 10,000 g/mol to about 100,000 g/mol, alternatively from about 20,000 g/mol to about 50,000 g/mol, alternatively from about 25,000 g/mol to about 45,000 g/mol, and the other of two or more polyvinyl alcohols may exhibit a weight average molecular weight of from about 105,000 g/mol to about 40,000,000 g/mol, alternatively from about 110,000 g/mol to about 20,000,000 g/mol, alternatively from about 120,000 g/mol to about 500,000 g/mol.

Non-limiting examples of fibrous-element forming polymeric structurant include water-soluble hydroxyl polymers, water-soluble thermoplastic polymers, water-soluble biodegradable polymers, water-soluble non-biodegradable polymers and mixtures thereof.

The one or more fibrous-element forming polymeric structurant materials may further comprise starch. In some examples, the one or more fibrous-element forming polymeric structurant materials may comprise one or more polyvinyl alcohols and starch.

The one or more fibrous-element forming materials may further comprise carboxymethyl cellulose. The one or more fibrous-element forming polymeric structurant materials may comprise one or more polyvinyl alcohols and carboxymethyl cellulose.

Surfactants

The melt composition and/or the dissolvable fibrous article and/or fibrous elements can contain from about 10% to about 90%, alternatively from about 20% to about 80%, alternatively from about 30% to about 75%, and alternatively from about 40% to about 70%, from about 45% to about 65%, of a surfactant system on by weight on a dry fibrous element basis and/or a dry dissolvable fibrous article basis.

Suitable anionic surfactants can include alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one embodiment, the anionic surfactant is sodium lauryl sulfate or sodium laureth sulfate.

In one embodiment, the anionic surfactant is at least one branched sulfate having the formula $CH_3—(CH_2)_z—CH(R^1)—CH_2—O—(CH_2CH(R^2)O)_y—SO_3M$; where z is from about 3 to about 14; $R^1$ represents H or a hydrocarbon radical comprising 1 to 4 carbon atoms, $R^2$ is H or $CH_3$; $R^1$ and $R^2$ are not both H; y is 0 to about 7; the average value of y is about 1 when y is not =0; and M is a mono-valent or di-valent, positively-charged cation. Examples of mono-valent positively charged cations include ammonium, sodium, potassium, triethanolamine cation, and examples of di-valent positively charged cations include magnesium. For the foregoing branched sulfates, "average value" means that whereas the composition may comprise molecules having a value of y of other than 1, the average value of y all molecules in the composition is about 1.

In some examples, the surfactant system can be substantially free or free of sulfate-based surfactants including alkyl sulfate and alkyl ether sulfate type of surfactant. Alternatively, the dissolvable fibrous article does not comprise any alkyl sulfate which comprises $C_{10}$-$C_{18}$ alkyl sulfate or any alkyl ether sulfate including alkyl glyceryl ether sulfates.

In some examples, the dissolvable fibrous article may not comprise any alkyl ether sulfates which have the formula:

$$RO(CH_2CH_2O)_nSO_3M$$

wherein R is an alkyl or alkenyl having 8 to 18 carbons, alternatively 12 to 18 carbons, n has an average value of greater than at least 0.5, alternatively between 2 and 3; and M is a solubilizing cation such as sodium, potassium, ammonium or substituted ammonium.

In some examples, the dissolvable fibrous article may not comprise any ammonium and sodium lauryl ether sulfates.

If the dissolvable fibrous article does contain alkyl sulfate and/or alkyl ether sulfate type of surfactant, its content of such a weight proportion of: alkyl sulfates or alkyl ether sulfate type surfactant is less than or equal to the sum of 0.6, alternatively less than or equal to the sum of 0.2, alternatively equal to 0.

Also, the product may be substantially free of or free of alkyl sulfate and alkyl ether sulfate type of surfactant, as described hereinbefore.

The one or more active agents comprise one or more surfactants, wherein the one or more surfactants comprise at least one glutamate surfactant according to the general formula (I):

(I)

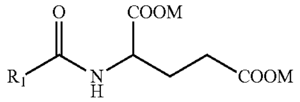

wherein Rican be saturated or unsaturated, straight or branched alkyl or alkenyl chain with from 5 to 20 carbon atoms, alternatively with from 7 to 17 carbon atoms, alternatively with from 9 to 13 carbon atoms; and M can be H, ammonium, triethanolammonium (TEA), sodium or potassium and mixtures thereof.

As set out above, the dissolvable fibrous article can be substantially free of or free of alkyl sulfate and alkyl ether sulfate type of surfactants.

The surfactant system can contain from an anionic primary surfactant. The article can contain from about 5% to about 70%, alternatively from about 10% to about 65%, alternatively from about 15% to about 55%, alternatively from about 20% to about 50% primary surfactant by weight of by weight on a dry fibrous element basis and/or a dry dissolvable fibrous article basis.

The surfactant system can contain an anionic primary surfactant. The article can contain from about 35% to about 100%, alternatively from about 40% to about 90%, alternatively from about 45% to about 85%, alternatively from about 50% to about 80%, alternatively from about 60% to about 75% primary surfactant by weight of the surfactant system on a dry fibrous element basis and/or a dry dissolvable fibrous article basis.

The primary anionic surfactant can comprise at least one glutamate surfactant. Non-limiting examples of glutamate surfactants can include sodium cocoyl glutamate, disodium cocoyl glutamate, potassium cocoyl glutamate, dipotassium cocoyl glutamate, ammonium cocoyl glutamate, diammonium cocoyl glutamate, sodium lauroyl glutamate, disodium lauroyl glutamate, potassium lauroyl glutamate, dipotassium lauroyl glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallowoyl glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallowoyl glutamate, sodium cocoyl/palmoyl/sunfloweroyl glutamate, sodium hydrogenated tallowoyl glutamate, sodium olivoyl glutamate, disodium olivoyl glutamate, sodium palmoyl glutamate, disodium palmoyl glutamate, TEA-cocoyl glutamate, TEA-hydrogenated tallowoyl glutamate, TEA-lauroyl glutamate, and mixtures thereof.

The at least one glutamate surfactant may be selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, sodium lauroyl glutamate, disodium lauroyl glutamate, potassium lauroyl glutamate, dipotassium lauroyl glutamate, sodium capryloyl glutamate, disodium capryloyl glutamate, potassium capryloyl glutamate, dipotassium capryloyl glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, TEA-cocoyl glutamate, and mixtures thereof In some examples, the at least one glutamate surfactant may be selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, TEA-cocoyl glutamate, and mixtures thereof.

The total level of the at least one glutamate surfactant may be from about 8% to about 100%, alternatively from about 8% to about 85%, alternatively from about 12% to about 70%, alternatively from about 17% to about 55%, and alternatively from about 20% to about 45%, by weight of the article. The glutamate level can be by weight on a dry fibrous element basis and/or a dry dissolvable fibrous article basis. The total level of the at least one glutamate surfactant can be from about 40% to about 100%, alternatively from about 40% to about 85%, alternatively from about 45% to about 80%, alternatively from about 50% to about 75%, by weight of the surfactant system on a dry fibrous element basis and/or a dry dissolvable fibrous article basis.

The primary anionic surfactant can comprise at least one alaninate surfactant. Non-limiting examples of alaninate surfactants can include sodium cocoyl alaninate, potassium cocoyl alaninate, ammonium cocoyl alaninate, sodium lauroyl alaninate, potassium lauroyl alaninate, sodium capryloyl alaninate, potassium capryloyl alaninate, sodium undecylenoyl alaninate, potassium undecylenoyl alaninate, sodium stearoyl alaninate, potassium stearoyl alaninate, sodium myristoyl alaninate, potassium myristoyl alaninate, sodium cocoyl/hydrogenated tallowoyl alaninate, sodium cocoyl/palmoyl/sunfloweroyl alaninate, sodium hydrogenated tallowoyl alaninate, sodium olivoyl alaninate, sodium palmoyl alaninate, TEA-cocoyl alaninate, TEA-hydrogenated tallowoyl alaninate, TEA-lauroyl glutamate, and mixtures thereof.

In some examples, the at least one alaninate surfactant may be selected from the group consisting of sodium cocoyl alaninate, potassium cocoyl alaninate, ammonium cocoyl alaninate, TEA-cocoyl alaninate, and mixtures thereof.

The one or more surfactants of the one or more active agents may also comprise a co-surfactant by weight of the composition, wherein the co-surfactant can be selected from the group consisting of an additional anionic surfactant, a non-ionic surfactant, an amphoteric surfactant, a zwitterionic surfactant, and mixtures thereof.

The article can optionally contain a co-surfactant. The total level of the co-surfactant can be from about 0.5% to about 50%, alternatively from about 2% to about 30%, alternatively from about 5% to about 25%, alternatively from about 7% to about 20%, by weight of the article on a dry fibrous element basis and/or a dry dissolvable fibrous article basis.

The total level of the co-surfactant can be from about 10% to about 65%, alternatively from about 15% to about 55%, alternatively from about 23% to about 50%, by weight of the surfactant system on a dry fibrous element basis and/or a dry dissolvable fibrous article basis.

The additional anionic surfactant may be selected from the group consisting of an isethionate surfactant, a sarcosinate surfactant, a glycinate surfactant, a sulfosuccinate surfactant, a sulfonate surfactant, a sulfoacetate surfactant, a glucose carboxylate surfactant, an alkyl ether carboxylate surfactant, a taurate surfactant, and mixtures thereof. Each anionic surfactant just listed above will be described in more details below.

The one or more surfactants of the one or more active agents may also comprise at least one isethionate surfactant according to the general formula (II):

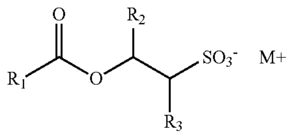

(II)

wherein $R_1$ can be a saturated or unsaturated, straight or branched, alkyl or alkenyl chain with from 6 to 30 carbon atoms, alternatively from 8 to 22 carbon atoms, alternatively from 9 to 18 carbon atoms, $R_2$ and $R_3$ are each independently H or (C1-$C_4$) alkyl, alternatively wherein (C1-$C_4$) alkyl can be methyl, and $M^+$ can be an alkali metal, alternatively lithium, sodium, potassium; or $M^+$ can be an alkali-earth metal, alternatively magnesium; or $M^+$ can be an ammonium or a substituted ammonium cation.

The isethionate surfactant may be selected from the group consisting of sodium lauroyl isethionate, sodium lauroyl methyl isethionate, sodium oleoyl isethionate, sodium oleoyl methyl isethionate, sodium stearoyl isethionate, sodium stearoyl methyl isethionate, sodium myristoyl isethionate, sodium myristoyl methyl isethionate, sodium palmitoyl isethionate, sodium palmitoyl methyl isethionate, sodium cocoyl isethionate, sodium cocoyl methyl isethionate, a blend of stearic acid and sodium cocoyl isethionate, ammonium cocoyl isethionate, ammonium cocoyl methyl isethionate, and mixtures thereof.

The isethionate surfactant may be selected from the group consisting of sodium lauroyl isethionate, sodium lauroyl methyl isethionate, sodium oleoyl isethionate, sodium stearoyl isethionate, sodium myristoyl isethionate, sodium palmitoyl isethionate, sodium cocoyl isethionate, ammonium cocoyl isethionate, and mixtures thereof.

The isethionate surfactant may be selected from the group consisting of sodium lauroyl isethionate, sodium lauroyl methyl isethionate, sodium stearoyl isethionate, sodium myristoyl isethionate, sodium cocoyl isethionate, ammonium cocoyl isethionate, and mixtures thereof.

The isethionate surfactant may be selected from the group consisting of sodium lauroyl isethionate, sodium cocoyl isethionate, ammonium cocoyl isethionate, and mixtures thereof.

Corresponding commercial products are available, for example, from the company Innospec under the trade name "Iselux®" and from Clariant or Uniquema under the trade names "Hostapon®" or "Arlatone®". Examples of other commercial fatty acyl isethionates that may be used can be Hostapon® surfactants from Clariant such as for sodium cocoyl isethionate: Hostapon® SCI-85C, Hostapon® SCI-78C, or a blend of stearic acid with sodium cocoyl isethionate: Hostapon® SCI-65C. Examples of other commercial fatty acyl isethionates that may be used can be "Jordapon®" surfactants from BASF such as Jordapon® CI prill or Jordapon® CI65; and sodium cocoyl isethionate from Yongan Daily Chemical Co. such as YA-SCI-85® or YA-SCI-65®.

The sarcosinate surfactant may have the general formula (III):

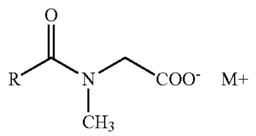

(III)

wherein R can be a saturated or unsaturated, straight or branched alkyl or alkenyl, alternatively alkyl chain with 7 to 17 carbon atoms, alternatively with 9 to 13 carbon atoms and $M^+$ can be H, a sodium, potassium, ammonium or triethanolammonium cation.

The sarcosinate surfactant may be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroyl glutamate/lauroyl sarcosinate, disodium lauroamphodiacetate, lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and mixtures thereof.

Alternatively, the sarcosinate surfactant may be selected from the group consisting of sodium lauroyl sarcosinate, sodium myristoyl sarcosinate, sodium cocoyl sarcosinate, and mixtures thereof.

The glycinate surfactant may be selected from the group consisting of sodium cocoyl glycinate, sodium lauroyl glycinate, and mixture thereof.

The sulfonate surfactant may be selected from the group consisting of alpha olefin sulfonates, linear alkylbenzene sulfonates, sodium laurylglucosides hydroxypropylsulfonate, and mixtures thereof.

The sulfoacetate surfactant may be selected from the group consisting of sodium lauryl sulfoacetate, ammonium lauryl sulfoacetate, and mixture thereof.

The glucose carboxylate surfactant may be selected from the group consisting of sodium lauryl glucoside carboxylate, sodium cocoyl glucoside carboxylate, and mixtures thereof.

The alkyl ether carboxylate surfactant may be selected from the group consisting of sodium laureth-4 carboxylate, laureth-5 carboxylate, laureth-13 carboxylate, sodium C12-13 pareth-8 carboxylate, sodium C12-15 pareth-8 carboxylate and mixtures thereof.

The taurate surfactant may be selected from the group consisting of sodium methyl cocoyl taurate, sodium methyl lauroyl taurate, sodium methyl oleoyl taurate, and mixtures thereof.

The anionic surfactant being not a glutamate surfactant may comprise a lactate or lactylate. Non-limiting example of lactates can include sodium lactate. Non-limiting examples of lactylates can include sodium lauroyl lactylate, sodium cocoyl lactylate, and mixture thereof.

The total level of additional anionic surfactant may be from about 0% to about 20% on a dry fibrous element basis and/or a dry dissolvable fibrous article basis. Alternatively, the total level of the anionic surfactant being not a glutamate surfactant may be from about 0.5% to about 15% on a dry fibrous element basis and/or a dry dissolvable fibrous article basis.

The one or more surfactants of the one or more active agents may comprise a non-ionic surfactant. The non-ionic surfactant may be selected from the group consisting alkyl polyglucoside, alkyl glycoside, acyl glucamide and mixtures thereof.

In that case, alkyl can be defined as a saturated or unsaturated, straight or branched alkyl chain with 6 to 30 carbon atoms, alternatively with 8 to 22 carbon atoms, alternatively with 9 to 18 carbon atoms. In that case, acyl can be defined as of formula R—C(O)—, wherein R can be a saturated or unsaturated, straight or branched alkyl or alkenyl, alternatively alkyl chain with 6 to 30 carbon atoms, alternatively with 8 to 22 carbon atoms, alternatively with 9 to 18 carbon atoms.

The alkyl glucoside may be selected from the group consisting of decyl glucoside, cocoyl glucoside, lauroyl glucoside, and mixtures thereof.

The acyl glucamide may be selected from the group consisting of lauroyl/myristoyl methyl glucamide, capryloyl/capryloyl methyl glucamide, cocoyl methyl glucamide and mixtures thereof. Alternatively, the non-ionic surfactant may be selected from the group consisting of cocoamide monoethanolamine, lauramide monoethanolamine, cocoyl glucoside, lauroyl glucoside, decyl glucoside, and mixtures thereof.

The total level of the non-ionic surfactant may be from about 0% to about 25% on a dry fibrous element basis and/or a dry dissolvable fibrous article basis. Alternatively, the total level of the non-ionic surfactant may be from about 0.1% to about 15% on a dry fibrous element basis and/or a dry dissolvable fibrous article basis. Alternatively, the total level of the non-ionic surfactant may be from about 0.5% to about 10% on a dry fibrous element basis and/or a dry dissolvable fibrous article basis.

Suitable amphoteric or zwitterionic surfactants can include those described in U.S. Pat. Nos. 5,104,646 and 5,106,609.

Amphoteric surfactants can include those that can be broadly described as derivatives of aliphatic secondary and tertiary amines in which an aliphatic radical can be straight or branched chain and wherein an aliphatic substituent can contain from 8 to 18 carbon atoms such that one carbon atom can contain an anionic water solubilizing group, e.g., carboxy, sulfonate, phosphate, or phosphonate. Examples of compounds falling within this definition can be sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378.

The amphoteric surfactant described herein may be selected from the group consisting of sodium lauroamphoacetate, sodium cocoamphoacetate, disodium lauroamphodiacetate, disodium cocodiamphoacetate, and mixtures thereof.

Zwitterionic surfactants suitable for use in the co-surfactants of the one or more active agents described herein may include those that are broadly described as derivatives of aliphatic quaternary ammonium, phosphonium, and sulfonium compounds, in which the aliphatic radicals can be straight or branched chains, and wherein one of the aliphatic substituents can contain from 8 to 18 carbon atoms and one can contain an anionic group, e.g., carboxy, sulfonate, phosphate, or phosphonate.

Hence, the one or more surfactants of the one or more active agents may comprise at least an amphoteric or zwitterionic surfactant selected from the group consisting of cocamidopropyl betaine, lauramidopropyl betaine, cocobetaine, lauryl betaine, lauryl hydroxysultaine, cocamidopropyl hydroxysultaine, coco-hydroxysultaine, coco-sultaine, lauryl sultaine, sodium cocoamphoacetate, disodium cocoamphodiacetate, sodium lauroamphoacetate, disodium lauroamphodiacetate, lauramine oxide, lauryl hydroxysultaine, and mixtures thereof.

Examples of betaine zwitterionic surfactants may include coco dimethyl carboxymethyl betaine, cocoamidopropyl betaine (CAPB), coco-betaine, lauryl amidopropyl betaine (LAPB), oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine, and mixtures thereof.

The total level of the zwitterionic surfactant may be from about 0.5% to about 20% on a dry fibrous element basis and/or a dry dissolvable fibrous article basis. Alternatively, the total level of the non-ionic surfactant may be from about 2% to about 15% on a dry fibrous element basis and/or a dry dissolvable fibrous article basis. Alternatively, the total level of the non-ionic surfactant may be from about 4% to about 13% on a dry fibrous element basis and/or a dry dissolvable fibrous article basis.

Cationic Polymers

The fibrous article can contain from about 0.05% to about 5% cationic polymer, from about 0.1% to about 3% cationic polymer, from about 0.2% to about 2.5% cationic polymer, from about 0.3% to about 2.0% cationic polymer, from about 0.4% to about 1.0% cationic polymer, on a dry fibrous element basis and/or a dry dissolvable fibrous article basis.

The cationic polymers can have a weight average molecular weight from about 500,000 g/mol to about 2.5 million g/mol, alternatively from about 500,000 g/mol to about 2 million g/mol, alternatively from about 500,000 g/mol to about 1.5 million, alternatively about 500,000 g/mol to about 1 million as measured by gel permeation chromatography. The cationic polymers can have a weight average molecular weight greater than 500,000 g/mol, alternatively greater than 1 million g/mol as measured by gel permeation chromatography.

The cationic polymers can have a weight average charge density greater than 0.2 meq/g, alternatively greater than 0.4 meq/g, alternatively 0.6 meg/g, alternatively 0.8 meg/g, alternatively 1 meq/g, alternatively 1.2 meq/g, alternatively 1.5 meg/g, alternatively 2 meg/g, alternatively greater than 3 meg/g, alternatively greater than 5 meg/g as measured according to the Charge Density Test Method. The cationic polymers can have a weight average charge density from about 0.4 meg/g to about 5 meg/g, alternatively from about 1 meg/g to about 3 meg/g, alternatively from about 1 meg/g to about 2.5 meg/g as measured according to the Charge Density Test Method.

A variety of cationic polymers can be used herein, and such cationic polymers are exemplified below. In some examples, the cationic polymer useful herein may be selected from Polyquaternium-6, Polyquaternium-7, Polyquaternium-10, cationic guars, and combinations thereof.

Cationic Guar Polymer

The hair care composition can comprise (a) a cationic guar polymer. Cationic guar polymers are cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of □(1-4) glycosidic linkages. The galactose branching arises by way of an □(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

The cationic guar polymer can have a weight average M.Wt. of less than 2.2 million g/mol, or from about 150 thousand g/mol to about 2 million g/mol, or from about 200 thousand to about 1.9 million g/mol, or from about 300 thousand to about 1.8 million g/mol, or from about 400 thousand to about 1.7 million g/mol, or from about 500,000 g/mol to about 1.6 million g/mol. The cationic guar polymer can have a weight average M.Wt. of greater than about 150,000 g/mol, alternatively greater than about 1 million g/mol, alternatively greater than about 1.5 million g/mol, alternatively greater than about 2 million g/mol, and alternatively greater than about 2.5 million g/mol.

The cationic guar polymer can have a weight average charge density of from about 0.2 meq/g to about 2.2 meg/g, or from about 0.3 meq/g to about 2.0 meg/g, or from about 0.4 meq/g to about 1.9 meg/g, or from about 0.5 meq/g to about 1.8 meg/g, or from about 0.6 meq/g to about 1.7 meg/g, or from about 0.6 meq/g to about 1.5 meq/g, or from about 0.6 meq/g to about 1.3 meg/g, and/or from about 0.7 meq/g to about 1.0 meg/g.

The cationic guar polymer may be formed from quaternary ammonium compounds. The quaternary ammonium compounds for forming the cationic guar polymer can conform to the general formula 1:

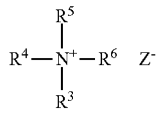

wherein where $R^3$, $R^4$ and $R^5$ are methyl or ethyl groups; $R^6$ is either an epoxyalkyl group of the general formula 2:

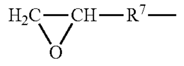

or $R^6$ is a halohydrin group of the general formula 3:

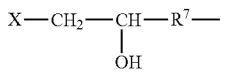

wherein $R^7$ is a $C_1$ to $C_3$ alkylene; X is chlorine or bromine, and Z is an anion such as Cl—, Br—, I— or $HSO_4$—.

The cationic guar polymer can conform to the general formula 4:

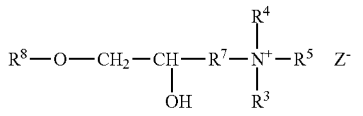

wherein $R^8$ is guar gum; and wherein $R^4$, $R^5$, $R^6$ and $R^7$ are as defined above; and wherein Z is a halogen. The cationic guar polymer can conform to Formula 5:

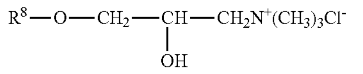

Suitable cationic guar polymers can include cationic guar gum derivatives, such as guar hydroxypropyltrimonium chloride. The cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a weight average molecular weight of 500,000 g/mol. Another guar hydroxypropyltrimonium chloride with a charge density of about 1.1 meq/g and a weight average molecular weight of about 500,000 g/mol is available from Ashland. A further guar hydroxypropyltrimonium chloride with a charge density of about 1.5 meq/g and a weight average molecular weight of about 500,000 g/mole is available from Ashland.

Other suitable guar hydroxypropyltrimonium chloride are: Hi-Care 1000, which has a charge density of about 0.7 meq/g and a weight average molecular weight of about 600,000 g/mole is available from Rhodia; N-Hance 3269 and N-Hance 3270, which have a charge density of about 0.7 meq/g and a weight average molecular weight of about 425,000 g/mol are available from Ashland; N-Hance 3271 which has a charge density of about 0.7 meq/g and a weight average molecular weight of about 500,000 g/mol and is available from Ashland; BF-13, which is a borate (boron) free guar of charge density of about 1.1 meq/g and weight average molecular weight of 10 about 800,000 and BF-17, which is a borate (boron) free guar of charge density of about 1.7 meq/g and M. W.t of about 800,000 both available from Ashland; N-Hance CG17 has a charge density of about 1.0 meq/g and a weight average molecular weight of about 1,600,000 g/mol and is available from Ashland; and N-Hance 3196 has a charge density of about 0.7 meq/g and a weight average molecular weight of 1,700,000 g/mol and is available from Ashland.

Cationic Synthetic Polymer

The hair care composition can include (b) a cationic synthetic polymer, wherein the cationic synthetic polymer can have a weight average M.Wt. of from about 1,000 g/mol to about 2.0 million g/mol, and wherein the cationic guar polymer can have a charge density of from about 2 meq/g to about 10 meq/g. The hair care composition can comprise a cationic synthetic polymer from about 0.01% to about 2.5% by total weight of the composition.

The cationic synthetic polymers may be formed from i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and cationic synthetic polymers having the following structure:

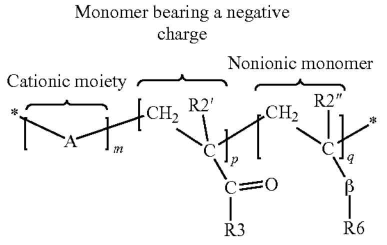

m ≥ 1
p = 0 or ≥ 1
q = 0 or ≥ 1
m ≥ p where A, may be one or more of the following cationic moieties:

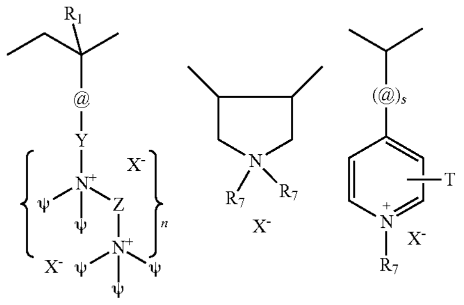

where @=amido, alkylamido, ester, ether, alkyl or alkylaryl;
where Y=C1-C22 alkyl, alkoxy, alkylidene, alkyl or aryloxy;
where □=C1-C22 alkyl, alkyloxy, alkyl aryl or alkyl aryloxy.
where Z=C1-C22 alkyl, alkyloxy, aryl or aryloxy;
where R1=H, C1-C4 linear or branched alkyl;
where s=0 or 1, n=0 or □1;
where T and R7=C1-C22 alkyl; and where X—=halogen, hydroxide, alkoxide, sulfate or alkylsulfate.

Where the monomer bearing a negative charge is defined by R2'=H, C1-C4 linear or branched alkyl and R3 as:

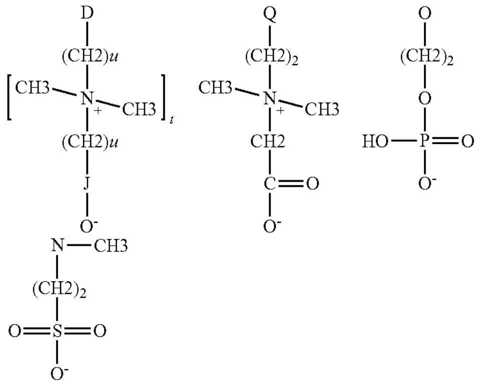

where D=O, N, or S;
where Q=$NH_2$ or O;
where u=1-6;
where t=0-1; and
where J=oxygenated functional group containing the following elements P, S, C.
Where the nonionic monomer is defined by R2"=H, C1-C4 linear or branched alkyl, R6=linear or branched alkyl, alkyl aryl, aryl oxy, alkyloxy, alkylaryl oxy and □ is defined as

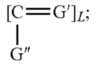

where G' and G" are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth) acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth) acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula $—NR_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X—) in association with the cationic synthetic polymers may be any known counterion so long as the polymers remain soluble or dispersible in water, in the hair care composition, or in a coacervate phase of the hair care composition, and so long as the counterions are physically and chemically compatible with the essential components of the hair care composition or do not otherwise unduly impair product performance, stability or aesthetics. Non limiting examples of such counterions include halides (e.g., chlorine, fluorine, bromine, iodine), sulfate and methylsulfate.

The cationic synthetic polymer can have a weight average M.Wt. of from about 1,500 g/mol to about 1.8 million g/mol, or from about 2,000 g/mol to about 1.7 million g/mol, or from about 3,000 g/mol to about 1.6 million g/mol, or from about 4,000 g/mol to about 1.5 million g/mol, or from about 5,000 g/mol to about 1.6 million g/mol, or from about 6,000 g/mol to about 1.5 million g/mol, or from about 7,000 g/mol to about 1.4 million g/mol, or from about 8,000 g/mol to about 1.4 million g/mol, or from about 9,000 g/mol to about 1.3 million g/mol, or from about 10,000 g/mol to about 1.2 million g/mol or from about 11,000 g/mol to about 1.1 million g/mol, or from about 25,000 g/mol to about 750,000 g/mol, or from about 50,000 g/mol to about 500,000 g/mol, or from about 75,000 g/mol to about 300,000 g/mol, and/or from about 100,000 g/mol to about 200,000 g/mol.

The cationic synthetic polymer can have a weight average charge density of from about 2.2 meq/g to about 9.5 meg/g, or from about 2.5 meq/g to about 8 meg/g, or from about 3 meq/g to about 8 meg/g, or from about 3.5 meq/g to about 7.5 meg/g, and/or from about 4 meq/g to about 7 meg/g.

The cationic synthetic polymer can comprise polydiallyldimethylammonium chloride (polyDADMAC). PolyDADMAC is also known as polyquaternium-6. Specific examples of polyDADMAC are Mirapol® 100 series from Solvay, Merquat™ 100 series from Lubrizol and Salcare® SC 30 from BASF. For example, Mirapol® 100s has a charge density of 6.2 meq/g and a weight average molecular weight of 150,000 g/mol, is available from Solvay. The cationic synthetic polymer can comprise a co-polymer of DADMAC and acrylamide which is known as Polyquaternium-7. Examples of polyquaternium-7 include Merquat 550, Merquat S, Mirapol 550, Salcare SC10, Salcare SC11 and Rheocare CC7.

The hair care composition may further comprise (c) a cationic non-guar galactomannan polymer, (d) a cationic starch polymer, (e) a cationic copolymer of acrylamide monomers and cationic monomers, (f) a cationic cellulose polymer or (g) a mixture of such polymers.

Cationic Non-Guar Galactomannan Polymers

The dispersion compositions can comprise a galactomannan polymer derivative having a mannose to galactose ratio of between 5:1 and 1:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and also is affected by climate. Non Guar Galactomannan polymer derivatives can have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and *Cassia* gum (5 parts mannose/1 part galactose).

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

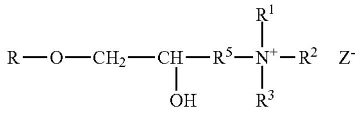

wherein R is the gum. The cationic galactomannan derivative can be a gum hydroxypropyltrimethylammonium chloride, which can be more specifically represented by the general formula 7:

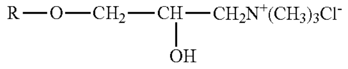

The galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose that is greater than about 4:1. The dispersion compositions may comprise a galactomannan polymer derivative, by weight, of the composition. The hair care compositions can comprise from about 0.05% to about 2%, by weight, of the composition, of a galactomannan polymer derivative.

(d) Cationically Modified Starch Polymer

The dispersion compositions can comprise water-soluble cationically modified starch polymers. As used herein, the term "cationically modified starch" refers to a starch to which a cationic group is added prior to degradation of the starch to achieve a relatively small weight average molecular weight, or wherein a cationic group is added after modification of the starch to achieve a desired weight average molecular weight. The definition of the term "cationically modified starch" also includes amphoterically modified starch. The term "amphoterically modified starch" refers to a starch hydrolysate to which a cationic group and an anionic group are added.

The dispersion compositions can comprise cationically modified starch polymers at a range of about 0.01% to about 10%, and/or from about 0.05% to about 5%, by weight, of the composition.

The cationically modified starch polymers disclosed herein can have a percent of bound nitrogen of from about 0.5% to about 4%.

The dispersion compositions can include starch polymers that is chemically modified by the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a relatively small weight average molecular weight or the cationic groups may be added after such modification.

The cationically modified starch polymers can generally have a degree of substitution of a cationic group from about 0.1 to about 7. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof.

Cationically modified starch polymers can be selected from degraded cationic maize starch, cationic tapioca, cationic potato starch, and mixtures thereof.

The starch, prior to degradation or after modification to achieve a relatively small weight average molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in compositions is available from known starch suppliers. Nonionic modified starch that could be further derivatized to a cationically modified starch as is known in the art can be suitable. Other suitable modified starch starting materials may be quaternized, as is known in the art, to produce the cationically modified starch polymer suitable for use in the invention.

Starch Degradation Procedure: A starch slurry is prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

Cationic Copolymer of an Acrylamide Monomer and a Cationic Monomer

The dispersion composition can comprise a cationic copolymer of an acrylamide monomer and a cationic monomer. The cationic copolymer can be a synthetic cationic copolymer of acrylamide monomers and cationic monomers.

The cationic copolymer can comprise:

(i) an acrylamide monomer of the following Formula AM:

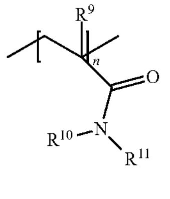

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula CM:

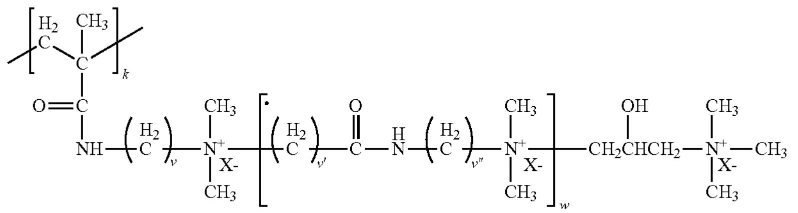

Formula CM where k=1, each of v, v', and v" is independently an integer of from 1 to 6, w is zero or an integer of from 1 to 10, and $X^-$ is an anion.

The cationic monomer can conform to Formula CM and where k=1, v=3 and w=0, z=1 and $X^-$ is $Cl^-$ to form the following structure:

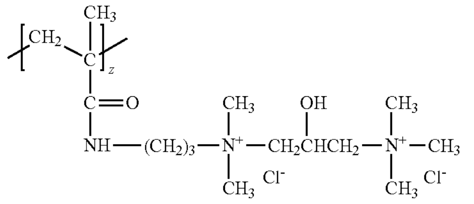

The above structure may be referred to as diquat. The cationic monomer can conform to Formula CM and wherein v and v" are each 3, v'=1, w=1, y=1 and $X^-$ is $Cl^-$, such as:

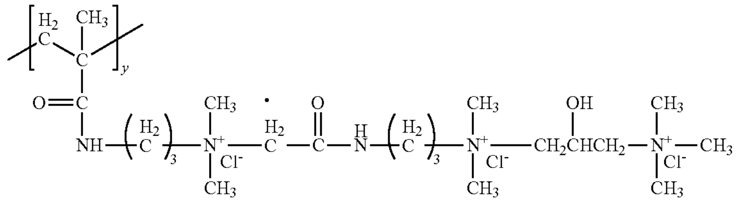

The above structure may be referred to as triquat.

The acrylamide monomer can be either acrylamide or methacrylamide.

The cationic copolymer (b) can be AM:TRIQUAT which is a copolymer of acrylamide and 1,3-Propanediaminium, N-[2-[[[dimethyl[3-[(2-methyl-1-oxo-2-propenyl)amino] propyl]ammonio]acetyl]amino]ethyl]2-hydroxy-N,N,N',N',N'-pentamethyl-, trichloride. AM:TRIQUAT is also known as polyquaternium 76 (PQ76). AM:TRIQUAT may have a charge density of 1.6 meq/g and a M.Wt. of 1.1 million g/mol.

The cationic copolymer can be an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer comprises a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer can be formed from (1) copolymers of (meth)acrylamide and cationic monomers based on (meth) acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. Cationized esters of the (meth)acrylic acid containing a quaternized N atom can be quaternized dialkylaminoalkyl (meth)acrylates with C1 to C3 in the alkyl and alkylene groups. The cationized esters of the (meth) acrylic acid containing a quaternized N atom are selected from the group consisting of: ammonium salts of dimethylaminomethyl (meth)acrylate, dimethylaminoethyl (meth) acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters of the (meth)acrylic acid containing a quaternized N atom can be dimethylaminoethyl acrylate, which may be quaternized with an alkyl halide, or with methyl chloride or benzyl chloride or dimethyl sulfate (ADAME-Quat). The cationic monomer when based on (meth)acrylamides can be quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

The cationic monomer based on a (meth)acrylamide is a quaternized dialkylaminoalkyl(meth)acrylamide with C1 to C3 in the alkyl and alkylene groups. The cationic monomer based on a (meth)acrylamide is dimethylaminopropylacrylamide, which is quaternized with an alkyl halide, especially methyl chloride or benzyl chloride or dimethyl sulfate.

The cationic monomer is a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer is hydrolysis-stable and the hydrolysis-stable cationic monomer is selected from the group consisting of: diallyldimethylammonium chloride and water-soluble, cationic styrene derivatives.

The cationic copolymer is a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer is formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer is a trimethylammoniopropylmethacrylamide chloride-N-Acrylamide copolymer, which is also known as AM:MAPTAC. AM:MAPTAC may have a charge density of about 1.3 meq/g and a M.Wt. of about 1.1 million g/mol. The cationic copolymer is AM:ATPAC. AM:ATPAC may have a charge density of about 1.8 meq/g and a M.Wt. of about 1.1 million g/mol.

Cationic Cellulose Polymers

Suitable cationic cellulose polymers are salts of hydroxyethyl cellulose reacted with trimethyl ammonium substituted epoxide, referred to in the industry (CTFA) as Polyquaternium 10 and available from Dow/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Extensional Aids

The fibrous elements can contain extensional aids. Nonlimiting examples of extensional aids can include polymers, other extensional aids, and combinations thereof.

In one example, the extensional aids have a weight average molecular weight of at least about 500,000 Da. The weight average molecular weight of the extensional aid is from about 500,000 Da to about 25,000,000 Da, alternatively from about 800,000 Da to about 22,000,000 Da, alternatively from about 1,000,000 Da to about 20,000,000 Da, and alternatively from about 2,000,000 Da to about 15,000,000 Da. The relatively high weight average molecular weight extensional aids can be utilized in some examples of the invention due to the ability to increase extensional melt viscosity and reducing melt fracture.

The extensional aid, when used in a meltblowing process, can be added to the composition in an amount effective to visibly reduce the melt fracture and capillary breakage of fibers during the spinning process such that substantially continuous fibers having relatively consistent diameter can be melt spun. Regardless of the process employed to produce fibrous elements and/or particles, the extensional aids, when used, can be present from about 0.001% to about 10%, by weight on a dry fibrous element basis and/or dry fibrous article basis, in one example, and in another example from about 0.005 to about 5%, by weight on a dry fibrous element basis and/or dry fibrous article basis, in yet another example from about 0.01 to about 1%, by weight on a dry fibrous element basis and/or dry fibrous article basis, and in another example from about 0.05% to about 0.5%, by weight on a dry fibrous element basis and/or dry fibrous article basis.

Non-limiting examples of polymers that can be used as extensional aids can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Nonlimiting examples of other extensional aids can include modified and unmodified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Optional Ingredients

The article can optionally comprise from about 5 wt. % to about 50 wt. % effervescent particles, in one embodiment from about 10 wt. % to about 30 wt. % effervescent particles, in one embodiment from about 5 wt. % to about 20 wt. % effervescent particles. Nonlimiting examples of effervescent particles comprise sodium bicarbonate and citric acid. In one embodiment ratio of sodium bicarbonate to citric acid from about 0.5:1 to about 5:1.

The article can optionally comprise from about 1 wt. % to about 25 wt. % plasticizer, in one embodiment from about 3 wt. % to about 20 wt. % plasticizer, in one embodiment from about 5 wt. % to about 15 wt. % plasticizer.

When present in the articles, non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol, isosorbide, glucamine, N-methylglucamine and other mono- and polyhydric relatively low weight average molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other relatively low weight average molecular weight esters (e.g., esters of C2-C10 alcohols and acids); and any other water soluble plasticizer known to one skilled in the art of the foods and plastics industries; and mixtures thereof. EP 0283165 B1 discloses suitable plasticizers, including glycerol derivatives such as propoxylated glycerol.

The article may comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials. Further non-limiting examples of optional ingredients include encapsulated perfumes, such as by β-cyclodetrins, polymer microcapsules, starch encapsulated accords and combinations thereof.

Suitable conditioning agents can optionally be added to the articles and can include high melting point fatty materials and silicone conditioning agents. Suitable materials are discussed in US 2008/0019935, US 2008/0242584 and US 2006/0217288.

Physical Properties of the Dissolvable Solid Fibrous Article (Structure)

For fibrous articles, the article comprises a significant number of dissolvable fibers with an average diameter less than about 150 micron, alternatively less than about 100 micron, alternatively less than about 10 micron, and alternatively less than about 1 micron with a relative standard deviation of less than 100%, alternatively less than 80%, alternatively less than 60%, alternatively less than 50%, such as in the range of 10% to 50%, for example. As set forth herein, the significant number means at least 10% of all the dissolvable fibers, alternatively at least 25% of all the dissolvable fibers, alternatively at least 50% of all the dissolvable fibers, alternatively at least 75% of all the dissolvable fibers. The significant number may be at least 99% of all the dissolvable fibers. Alternatively, from about 50% to about 100% of all the dissolvable fibers may have an average diameter less than about 10 micron. The dissolvable fibers produced by the method of the present disclosure have a significant number of dissolvable fibers with an average diameter less than about 1 micron, or sub-micron fibers. In an embodiment, Dissolvable Solid article may have from about 25% to about 100% of all the dissolvable fibers with an average diameter less than about 1 micron, alternatively from about 35% to about 100% of all the dissolvable fibers with an average diameter less than about 1 micron, alternatively from about 50% to about 100% of all the dissolvable fibers with an average diameter less than about 1 micron, and alternatively from about 75% to about 100% of all the dissolvable fibers with an average diameter less than about 1 micron.

The percent porosity of the dissolvable solid article is at least about 25%, alternatively at embodiment at least about 50%, alternatively at least about 60%, alternatively at least about 70% and alternatively at least about 80%. The porosity of the dissolvable solid article is not more than about 99%, alternatively not more than about 98%, alternatively not more than about 95%, and alternatively not more than about 90%. Porosity of an article is determined according to the procedure set forth in the definition of "porosity" above.

A range of effective sizes of pores can be accommodated. The pore size distribution through the article cross-section may be symmetric or asymmetric.

The article can be flexible and have a distance to maximum force value of from about 6 mm to about 30 mm. The distance to maximum force value from about 7 mm to about 25 mm, alternatively from about 8 mm to about 20 mm, and alternatively from about 9 mm to about 15 mm.

The article can be characterized in one aspect by its Specific Surface Area. The article can have a Specific Surface Area of from about 0.03 $m^2/g$ to about 0.25 $m^2/g$, alternatively from about 0.035 $m^2/g$ to about 0.22 $m^2/g$, alternatively from about 0.04 $m^2/g$ to about 0.19 $m^2/g$, and alternatively from about 0.045 $m^2/g$ to about 0.16 $m^2/g$.

The article can be a flat, flexible article in the form of a pad, a strip, or tape and having a thickness of from about 0.5 mm to about 10 mm, alternatively from about 1 mm to about 9 mm, alternatively from about 2 mm to about 8 mm, and alternatively from about 3 mm to about 7 mm as measured by the below methodology. The article can be a sheet having a thickness from about 5 mm to about 6.5 mm. Alternatively, two or more sheets are combined to form an article with a thickness of about 5 mm to about 10 mm.

The article can have a basis weight of from about 200 $grams/m^2$ to about 2,000 $grams/m^2$, alternatively from about 400 $g/m^2$ to about 1,200 $g/m^2$, alternatively from about 600 $g/m^2$ to about 2,000 $g/m^2$, and alternatively from about 700 $g/m^2$ to about 1,500 $g/m^2$.

The article can have a dry density of from about 0.08 $g/cm^3$ to about 0.40 $g/cm^3$, alternatively from about 0.08 $g/cm^3$ to about 0.38 $g/cm^3$, alternatively from about 0.10 $g/cm^3$ to about 0.25 $g/cm^3$, and alternatively from about 0.12 $g/cm^3$ to about 0.20 $g/cm^3$.

The article can have a hand dissolution value, as determined by the Hand Dissolution Method, described hereafter, of less than about 20 strokes, alternatively less than about 15 strokes, alternatively less than 12 strokes.

Non-limiting examples of other fibrous articles suitable for the present invention are disclosed in U.S. Pat. Nos.

8,980,816 and 9,139,802, U.S. Pub. No. 2013/0171421, and U.S. application Ser. No. 16/912,876 are hereby incorporated by reference.

Methods of Use

The dissolvable solid substrates described herein may be used for cleaning and/or treating hair, hair follicles, skin, teeth, and the oral cavity. The method for treating these consumer substrates may comprise the steps of: a) applying an effective amount of the Structure to the hand, b) wetting the Structure with water to dissolve the solid, c) applying the dissolved material to the target consumer substrate such as to clean or treat it, and d) rinsing the diluted treatment composition from the consumer substrate. These steps can be repeated as many times as desired to achieve the desired cleansing and or treatment benefit.

A method useful for providing a benefit to hair, hair follicles, skin, teeth, and/or the oral cavity, includes the step of applying a composition according to the first embodiment to these target consumer substrates in need of regulating.

Alternatively, a useful method for regulating the condition of hair, hair follicles, skin, teeth, the oral cavity, includes the step of applying one or more compositions described herein to these target consumer substrates in need of regulation.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.5 grams to about 10 grams, alternatively from about 1.0 grams to about 5 grams, and alternatively from about 1.5 grams to about 3 grams.

Product Types and Articles of Commerce

Non-limiting examples of products that utilize the dissolvable solid structures include hand cleansing substrates, teeth cleaning or treating substrates, oral cavity substrates, hair shampoo or other hair treatment substrates, body cleansing substrates, shaving preparation substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

The dissolvable solid structure can a personal care product, which can include a hair care product. In some examples the hair care product can be a rinse-off hair care product. In other examples, the hair care product can be a rinse-off hair care product containing non-sulfate surfactant.

Described herein is an article of commerce comprising one or more dissolvable solid structures described herein, and a communication directing a consumer to dissolve the Structure and apply the dissolved mixture to hair, hair follicles, skin, teeth, the oral cavity, to achieve a benefit to the target consumer substrate, a rapidly lathering foam, a rapidly rinsing foam, a clean rinsing foam, and combinations thereof. The communication may be printed material attached directly or indirectly to packaging that contains the dissolvable solid structure or on the dissolvable solid structure itself. Alternatively, the communication may be an electronic or a broadcast message that is associated with the article of manufacture. Alternatively, the communication may describe at least one possible use, capability, distinguishing feature and/or property of the article of manufacture.

Method for Making Fibrous Elements and Articles

The fibrous elements may be made by any suitable process. A non-limiting example of a suitable process for making the fibrous elements is described below.

Figure 1:
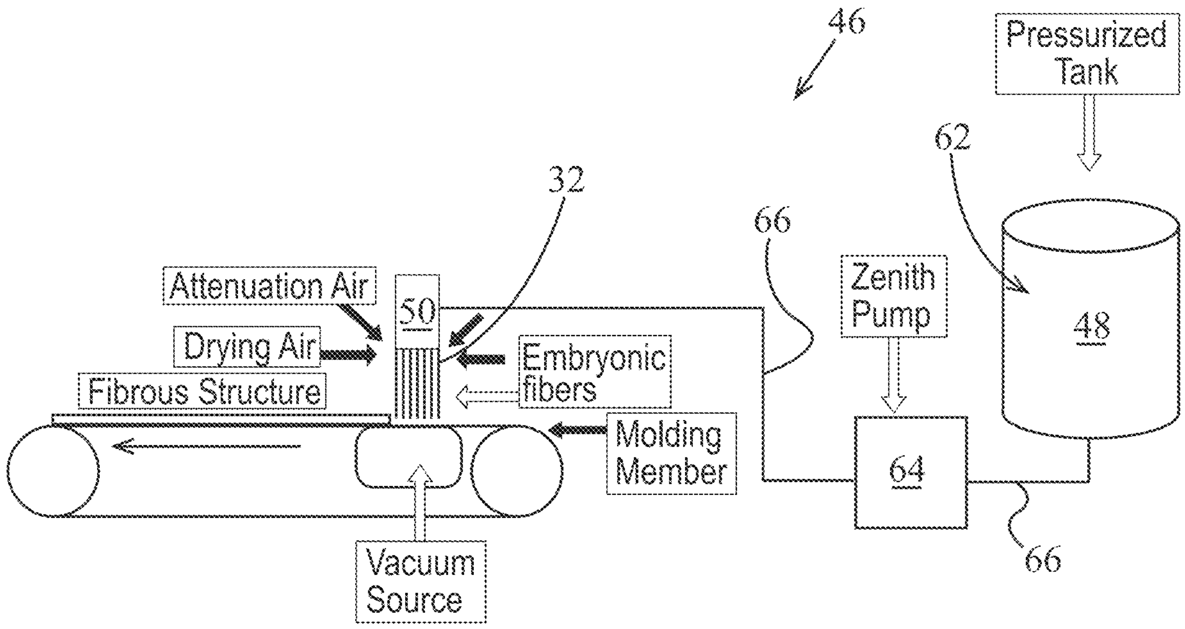
FIG. 1 is a schematic representation of an example of a process for making fibrous elements of the present invention.
Figure 2:
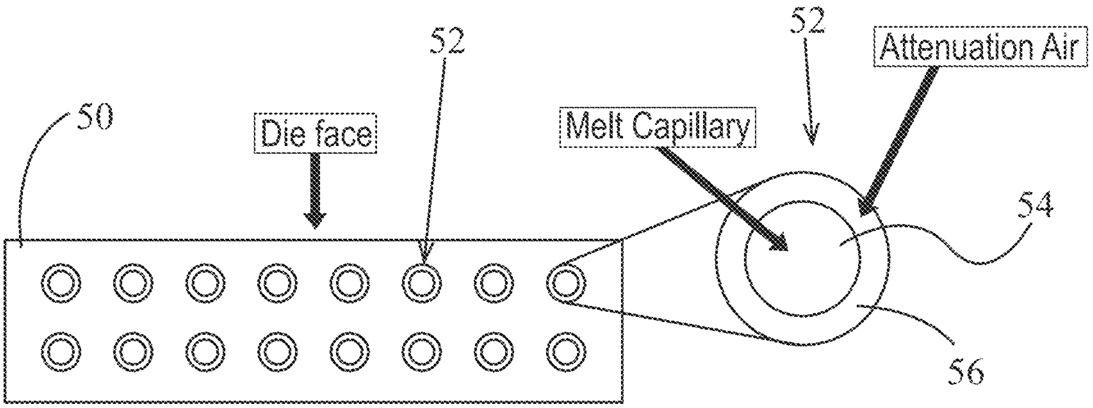
FIG. 2 is a schematic representation of an example of a die with a magnified view used in the process of FIG. 2.

In one example, as shown in FIGS. 1 and 2 a method 46 for making a fibrous element 32 according to the present invention comprises the steps of:

a. providing a filament-forming composition 48; and
b. spinning the filament-forming composition 48, such as via a spinning die 50, into one or more fibrous elements 32, such as filaments As shown in FIG. 2, the spinning die 50 may comprise a plurality of fibrous element-forming holes 52 that include a melt capillary 54 encircled by a concentric attenuation fluid hole 56 through which a fluid, such as air, passes to facilitate attenuation of the filament-forming composition 48 into a fibrous element 32 as it exits the fibrous element-forming hole 52.

In one example, during the method for making fibrous elements, any volatile solvent, such as water, present in the filament-forming composition 48 is removed, such as by drying, as the fibrous element 32 is formed. In one example, greater than 30% and/or greater than 40% and/or greater than 50% and/or greater than 60% of the weight of the filament-forming composition's volatile solvent, such as water, is removed during the spinning step, such as by drying the fibrous element being produced.

In one example, when the fibrous element exits the fibrous element-forming hole 52, they are collected on a belt above a vacuum source called the forming zone. The fibrous elements can remain on the forming zone for the following times and temperatures: from about 150° F. (65.6° C.) to about 160° F. (71.1° C.) for about 50 to about 60 seconds and/or from about 170° F. (65.6° C.) to about 180° F. (82.2° C.) for about 30 to about 40 seconds and/or from about 200° F. (93.3° C.) to about 215° F. (101.7° C.) for about 5 to about 20 seconds.

In one example, to enable the balance of solvent evaporation, dwell time, and heat exposure it is apparent that melt spinning temperature could be from about 70° F. to about 95° F. while enabling drying with heat such as about 340° F. (171.1° C.) to about 350° F. (176.7° C.) for about 50 to about 60 seconds or from about 390° F. (198.9° C.) to about 400° F. (204° C.) for about 30 to about 40 seconds or 415° F. (212.8° C.) to 470° F. (243.3° C.) for about 5 to about 20 seconds.

The filament-forming composition is spun into one or more fibrous elements and/or particles by any suitable spinning process, such as meltblowing, spunbonding, electro-spinning, and/or rotary spinning. In one example, the filament-forming composition is spun into a plurality of fibrous elements and/or particles by meltblowing. For example, the filament-forming composition may be pumped from a tank to a meltblown spinnerette. Upon exiting one or more of the filament-forming holes in the spinnerette, the filament-forming composition is attenuated with air to create one or more fibrous elements and/or particles. The fibrous elements and/or particles may then be dried to remove any remaining solvent used for spinning, such as the water.

The fibrous elements and/or particles may be collected on a belt, such as a patterned belt to form a fibrous article comprising the fibrous elements and/or particles.

Test Methods

Basis Weight Measurement

In general, basis weight of a material or article (including the dissolvable solid structure) is measured by first cutting the sample to a known area, using a die cutter or equivalent, then measuring & recording the weight of the sample on a top-loading balance with a minimum resolution of 0.01 g, then finally by calculating the basis weight as follows:

Basis Weight ($g/m^2$)=weight of basis weight pad (g)

$$\text{Basis Weight}\left(\frac{g}{m^2}\right)=\frac{\text{Weight of pad (g)}\times 10{,}000\ \frac{cm^2}{m^2}}{\text{area of pad }(cm^2)}$$

Suitable pad sample sizes for basis weight determination are >10 $cm^2$ and should be cut with a precision die cutter having the desired geometry. If the dissolvable solid structure to be measured is smaller than 10 $cm^2$, a smaller sampling area can be sued for basis weight determination with the appropriate changes to calculation.

In the present examples, basis weight was calculated based on the full dissolvable solid structure having a known area of 17.28 $cm^2$. Thus, the basis weight calculation becomes:

$$\text{Basis Weight}\left(\frac{g}{m^2}\right)=\frac{\text{Weight of pad (g)}\times 10{,}000\ \frac{cm^2}{m^2}}{17.28\ cm^2}$$

Hand Dissolution Test Method

Materials Needed:

Dissolvable solid structures to be tested: 3-5 dissolvable solid structure s (finished product samples) are tested so that an average of the number of strokes for each if the individual dissolvable solid structure samples is calculated and recorded as the Average Hand Dissolution value for the dissolvable solid structure. For this method, the entire consumer saleable or consumer use dissolvable solid structure is tested. If the entire consumer saleable or consumer use dissolvable solid structure has a footprint greater than 50 cm2, then first cut the dissolvable solid structure to have a footprint of 50 $cm^2$.

Nitrile Gloves 10 cc syringe

Plastic Weigh boat (~3 in ×3 in)

100 mL Glass beaker

Water (City of Cincinnati Water or equivalent having the following properties: Total Hardness=155 mg/L as CaCO2; Calcium content=33.2 mg/L; Magnesium content=17.5 mg/L; Phosphate content=0.0462 mg/L)

Water used is 7 gpg hardness and 40° C.+/−5° C.

Protocol:

1. Add 80 mL of water to glass beaker. Add 300-500 ml of water to glass beaker.
2. Heat water in beaker until water is at a temperature of 40° C.+/−5° C.
3. Transfer 10 mL of the water from the beaker into the weigh boat via the syringe.
4. Within 10 seconds of transferring the water to the weigh boat, place dissolvable solid structure sample in palm of gloved hand (hand in cupped position in non-dominant hand to hold dissolvable solid structure sample).
5. Using dominant hand, add water quickly from the weigh boat to the dissolvable solid structure sample and allow to immediately wet for a period of 5-10 seconds.
6. Rub with opposite dominant hand (also gloved) in 2 rapid circular strokes.
7. Visually examine the dissolvable solid structure sample in hand after the 2 strokes. If dissolvable solid structure sample is completely dissolved, record number of strokes=2 Dissolution Strokes. If not completely dissolved, rub remaining dissolvable solid structure sample for 2 more circular strokes (4 total) and observe degree of dissolution. If the dissolvable solid structure sample contains no solid pieces after the 2 additional strokes, record number of strokes=4 Dissolution Strokes. If after the 4 strokes total, the dissolvable solid structure sample still contains solid pieces of un-dissolved dissolvable solid structure sample, continue rubbing remaining dissolvable solid structure sample in additional 2 circular strokes and check if there are any remaining solid pieces of dissolvable solid structure sample after each additional 2 strokes until dissolvable solid structure sample is completely dissolved or until reaching a total of 30 strokes, whichever comes first. Record the total number of strokes. Record 30 Dissolution Strokes even if solid dissolvable solid structure sample pieces remain after the maximum of 30 strokes.
8. Repeat this process for each of the additional 4 dissolvable solid structure samples.
9. Calculate the arithmetic mean of the recorded values of Dissolution Strokes for the 5 individual dissolvable solid structure samples and record as the Average Hand Dissolution Value for the dissolvable solid structure. The Average Hand Dissolution Value is reported to the nearest single Dissolution Stroke unit.

Fibrous Structures—Fiber Diameter

For fibrous Structures, the diameter of dissolvable fibers in a sample of a web is determined by using a Scanning Electron Microscope (SEM) or an Optical Microscope and image analysis software. A magnification of 200 to 10,000 times is chosen such that the fibers are suitably enlarged for measurement. When using the SEM, the samples are sputtered with gold or a palladium compound to avoid electric charging and vibrations of the fibers in the electron beam. A manual procedure for determining the fiber diameters is used from the image (on monitor screen) taken with the SEM or the optical microscope. Using a mouse and a cursor tool, the edge of a randomly selected fiber is sought and then measured across its width (i.e., perpendicular to fiber direction at that point) to the other edge of the fiber. A scaled and calibrated image analysis tool provides the scaling to get actual reading in microns (μm). Several fibers are thus randomly selected across the sample of the web using the SEM or the optical microscope. At least two specimens from the web (or web inside a product) are cut and tested in this manner. Altogether at least 100 such measurements are made and then all data are recorded for statistical analysis. The recorded data are used to calculate average (mean) of the fiber diameters, standard deviation of the fiber diameters, and median of the fiber diameters. Another useful statistic is the calculation of the amount of the population of fibers that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micron diameter or %-submicron, for example. We denote the measured diameter (in microns) of an individual circular fiber as di.

In case the fibers have non-circular cross-sections, the measurement of the fiber diameter is determined as and set equal to the hydraulic diameter which is four times the cross-sectional area of the fiber divided by the perimeter of the cross of the fiber (outer perimeter in case of hollow fibers). The number-average diameter, alternatively average diameter is calculated as, $d_{num}$ $$\frac{\sum_{i=1}^{n} d_i}{n}$$

Water Content Test Method

The water (moisture) content present in a fibrous element and/or particle and/or fibrous article is measured using the following Water Content Test Method. A fibrous element and/or particle and/or fibrous article or portion thereof ("sample") in the form of a pre-cut sheet is placed in a conditioned room at a temperature of 22° C.±2° C. and a relative humidity of 42%±4% for at least 24 hours prior to testing. Each fibrous article sample has an area of at least 4 square inches, but small enough in size to fit appropriately on the balance weighing plate. Under the temperature and humidity conditions mentioned above, using a balance with at least four decimal places, the weight of the sample is recorded every five minutes until a change of less than 0.5% of previous weight is detected during a 10-minute period. The final weight is recorded as the "equilibrium weight". Within 10 minutes, the samples are placed into the forced air oven on top of foil for 24 hours at 22° C.±2° C. and a relative humidity of 42%±4% for drying. After the 24 hours of drying, the sample is removed and weighed within 15 seconds. This weight is designated as the "dry weight" of the sample.

The water (moisture) content of the sample is calculated as follows:

% Water in sample=100%×(Equilibrium weight of sample−Dry weight of sample)

Dry weight of sample

The % Water (moisture) in sample for 3 replicates is averaged to give the reported % Water (moisture) in sample. Report results to the nearest 0.1%.

Combinations

A dissolvable solid fibrous shampoo article comprising a plurality of fibrous elements, comprising:
- a. from about 1% to about 50%, by weight on a dry article basis, of a polymeric structurant;
- b. from about 0.1% to about 5% by weight on a dry article basis, of a cationic polymer;
- c. from about 20% to about 70%, by weight on a dry article basis, of a surfactant;
- d. from about 5.5% to about 20%, by weight on a dry article basis, of a salt comprising an inorganic salt and an organic salt, wherein the inorganic salt is contained at a level of from about 0% to less than 5% (excluding 5%) by weight on a dry article basis, and wherein the organic salt is contained at a level of from about 1% to about 18% by weight on a dry article basis; wherein the plurality of fibrous elements are intertangled or otherwise associated with one another to form the fibrous article.

The article of the preceding feature, comprising alternatively from about 7% to about 18%, alternatively from about 8% to about 16% by weight on a dry article basis, of the salt comprising the inorganic salt and the organic salt.

The article of any of the preceding features, wherein the organic salt is contained at a level of alternatively from about 2% to about 16%, alternatively from about 3% to about 14%, alternatively from about 5.2% to about 14% by weight on a dry article basis.

The article of any of the preceding features, wherein the inorganic salt is contained at a level of alternatively from about 1.2% to about 4.9%, alternatively from about 1.5% to about 4.8% by weight on a dry article basis.

The article of any of the preceding features, wherein the organic salt is a salt of an organic acid.

The article of any of the preceding features, wherein the organic acid has an average molecular weight of from about 80 to about 400 daltons, alternatively from about 80 to about 200 daltons, alternatively from about 90 to about 150 daltons.

The article of any of the preceding features, wherein the organic acid is selected from the group consisting of lactic acids, citric acid, oxalic acid, malonic acid, tartronic acid, fumaric acid, maleic acid, malic acid, and tartaric acid, and combinations thereof, preferably lactic acid.

The article of any of the preceding features, wherein the surfactant is surfactant system comprising:
- i. from about 35% to about 90%, by weight of the surfactant system on a dry article basis, of a primary anionic surfactant; and
- ii. from about from about 0% to about 65%, by weight of the surfactant system on a dry article basis, of a co-surfactant; wherein the surfactant system is substantially free of sulfate-based surfactants.

The article of any of the preceding features, wherein the primary anionic surfactant comprises a glutamate surfactant selected from sodium cocoyl glutamate, disodium cocoyl glutamate, potassium cocoyl glutamate, dipotassium cocoyl glutamate, ammonium cocoyl glutamate, diammonium cocoyl glutamate, TEA-cocoyl glutamate, or combinations thereof or an alaninate surfactant selected from sodium cocoyl alaninate, sodium lauroyl alaninate, sodium N-dodecanoyl-1-alaninate, or combinations thereof.

The article of any of the preceding features, wherein the polymeric structurant is selected from carboxymethyl cellulose, starch, polyvinyl alcohol, and combinations thereof.

The article of any of the preceding features, wherein the fibrous elements are formed by a homogeneous mixture comprising: the polymeric structurant; the cationic polymer; the surfactant; and the salt comprising the inorganic salt and the organic salt.

The article of any of the preceding features, wherein the cationic polymer is selected from Polyquaternium-6, Polyquaternium-7, Polyquaternium-10, cationic guars, and combinations thereof.

The article of any of the preceding features, wherein the article comprises a hand dissolution value of less than 15 strokes according to the Hand Dissolution Test Method.

EXAMPLES

The following are non-limiting examples of the shampoo compositions described herein. It will be appreciated that other modifications of the present invention within the skill of those in the art can be undertaken without departing from the spirit and scope of this invention.

All parts, percentages, and ratios herein are by weight unless otherwise specified. Some components may come from suppliers as dilute solutions. The amount stated reflects the weight percent of the added material, unless otherwise specified.

TABLE 1

Compositions of Dissolvable Solid Fibrous Shampoo Articles (Active level wt % on dry basis)

| | Ex. 1 | Ex. 2 | Comp. Ex. i | Comp. Ex. ii | Comp. Ex. iii | Comp. Ex. iv |
|---|---|---|---|---|---|---|
| Polyvinyl alcohol (PVA) *1 | 30.2 | 31.4 | 30.2 | 30.8 | 31.8 | 32.6 |
| Disodium cocoyl glutamate | 42.4 | 27.0 | 37.3 | 38.9 | 44.8 | 46.4 |
| Sodium cocoyl alaninate | 11.6 | 26.6 | 15.1 | 11.6 | 12.2 | 12.5 |
| EDTA | 0.2 | 0.2 | 0.2 | 0.2 | 0.2 | 0.2 |
| Sodium Lactate | 6.1 | 4.7 | 5.2 | 5.2 | 0 | 0 |
| Sodium Chloride | 4.7 | 4.9 | 6.5 | 7.1 | 3.7 | 0 |
| Polyquaternium-6 *2 | 0.5 | 0.5 | 0.5 | 0.5 | 0.5 | 0.5 |
| Polyquaternium-10 *3 | 0.5 | 0.5 | 0.5 | 0.5 | 0.5 | 0.5 |
| Moisture and other impurities | Q.S. | Q.S. | Q.S. | Q.S. | Q.S. | Q.S. |
| Fiber spinnability | Good | Good | Fair | Fair | Good | Good |
| Average Hand Dissolution Value | 8 | 9 | 12 | 12 | 22 | >30 |

*1 50:50 blend of Poval 32-80 having a weight average MW of 170,000 and Poval 3-80 having a weight average MW of 25,000 from Kuraray ®
*2 Polyquaternium-6, PolyDADMAC, MW of 150,000, CD of 6.2, trade name: Mirapol ® 100 s, 31.5% active, 40% solids from Solvay ®
*3 Polyquaternium-10, UCARE ™ Polymer JR-30M from Amerchol ®, MW of 2,000,000, CD of 1.25

The dissolvable solid articles of Ex.1 and Ex. 2 are inventive examples, and the dissolvable solid articles of Comp. Ex. 1 through Comp. Ex. iv are comparative examples. The inventive examples provide dissolvable solid fibrous shampoo articles having an adequate strength during manufacturing while not slowing down the dissolution of the structure during usage, compared to comparative examples.

Ingredients

Fiber Spinnability

Mechanical strength during manufacturing the dissolvable solid fibrous structure is evaluated by fiber spinnability when forming fibrous elements. The dissolvable solid fibrous structure is formed by a plurality of fibrous elements. Fiber spinnability, in Table 1, was determined by spinning a fibrous element-forming composition comprising the above ingredients in the table @ about 40% total solids (balance being water), according to the Method for Making Fibrous Elements and Articles described herein. The levels of the ingredients in such fibrous element-forming composition are adjusted such that the ingredients have the levels defined above in the dissolvable solid fibrous structure.

Good: Continuous filaments could be formed without breaking and/or retracting, and the continuous filaments could be collected on the belt.

Fair: Continuous filaments are not formed with some filaments are broken before lying on the belt. This can cause some difficulties to make articles with expected physical properties/performance, and/or cause some difficulties in latter manufacturing process.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dissolvable solid fibrous shampoo article comprising a plurality of fibrous elements, comprising:

a. from about 1% to about 50%, by weight on a dry article basis, of polyvinyl alcohol;

b. from about 0.1% to about 5% by weight on a dry article basis, of one or more cationic polymers chosen from Polyquaternium-6, Polyquaternium-7, Polyquaternium-10, cationic guars, or a combination mixtures thereof;

c. from about 20% to about 70%, by weight on a dry article basis, of a surfactant system comprising a glutamate surfactant and an alaninate surfactant, wherein the surfactant system is free of sulfate-based surfactants;

d. from about 5.5% to about 20%, by weight on a dry article basis, of at least two salts comprising:

i. sodium chloride; wherein the composition comprises less than 5% by weight on a dry article basis, of the sodium chloride;

ii. from about 1% to about 18% by weight on a dry article basis, of sodium lactate;

wherein the plurality of fibrous elements are intertangled or otherwise associated with one another to form the fibrous article.

2. The article of claim 1, wherein the fibrous elements comprise from about 7% to about 18% by weight on a dry article basis, of the at least two salts.

3. The article of claim 2, wherein the fibrous elements comprise from about 8% to about 16% by weight on a dry article basis, of the at least two salts.

4. The article of claim 1, wherein the salt comprises from about 2% to about 16% by weight on a dry article basis, of the sodium lactate.

5. The article of claim 4, wherein the salt comprises from about 3% to about 14%, by weight on a dry article basis, of the sodium lactate.

6. The article of claim 5, wherein the salt comprises from about 5.2% to about 14%, by weight on a dry article basis, of the sodium lactate.

7. The article of claim 1, wherein the salt comprises from about 1.2% to about 4.9%, by weight on a dry article basis, of the sodium chloride.

8. The article of claim 1, wherein the glutamate surfactant is chosen from sodium cocoyl glutamate, disodium cocoyl glutamate, potassium cocoyl glutamate, dipotassium cocoyl glutamate, ammonium cocoyl glutamate, diammonium cocoyl glutamate, TEA-cocoyl glutamate, or combinations thereof or an alaninate surfactant selected from sodium cocoyl alaninate, sodium lauroyl alaninate, sodium N-dodecanoyl-1-alaninate, or mixtures thereof.

9. The article of claim 1, wherein the alaninate surfactant is chosen from sodium cocoyl alaninate, potassium cocoyl alaninate, ammonium cocoyl alaninate, sodium lauroyl alaninate, potassium lauroyl alaninate, sodium capryloyl alaninate, potassium capryloyl alaninate, sodium undecylenoyl alaninate, potassium undecylenoyl alaninate, sodium stearoyl alaninate, potassium stearoyl alaninate, sodium myristoyl alaninate, potassium myristoyl alaninate, sodium cocoyl/hydrogenated tallowoyl alaninate, sodium cocoyl/palmoyl/sunfloweroyl alaninate, sodium hydrogenated tallowoyl alaninate, sodium olivoyl alaninate, sodium palmoyl alaninate, TEA-cocoyl alaninate, TEA-hydrogenated tallowoyl alaninate, TEA-lauroyl glutamate, or mixtures thereof.

10. The article of claim 1, wherein the glutamate surfactant comprises disodium cocoyl glutamate and the alaninate surfactant comprises sodium cocoyl alaninate.

11. The article of claim 1, wherein the composition comprises from about from about 20% to about 40% of the polyvinyl alcohol.

12. The article of claim 1, wherein the article comprises a hand dissolution value of less than 15 strokes according to the Hand Dissolution Test Method.

* * * * *